US011298316B2

(12) United States Patent
Abbott et al.

(10) Patent No.: US 11,298,316 B2
(45) Date of Patent: *Apr. 12, 2022

(54) TOPICAL COPPER ION TREATMENTS AND METHODS OF TREATMENT USING TOPICAL COPPER ION TREATMENTS IN THE ORAL-RESPIRATORY-OTIC AREAS OF THE BODY

(71) Applicant: CDA Research Group, Inc., Pittsburgh, PA (US)

(72) Inventors: ChunLim Abbott, Pittsburgh, PA (US); Dominic C. Abbott, Pittsburgh, PA (US)

(73) Assignee: CDA RESEARCH GROUP, INC., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/231,764

(22) Filed: Apr. 15, 2021

(65) Prior Publication Data

US 2021/0228476 A1 Jul. 29, 2021

Related U.S. Application Data

(63) Continuation of application No. 13/842,310, filed on Mar. 15, 2013, now Pat. No. 11,007,143.

(51) Int. Cl.
| | |
|---|---|
| *A61K 9/00* | (2006.01) |
| *A61K 33/34* | (2006.01) |
| *A61K 8/19* | (2006.01) |
| *A61K 9/02* | (2006.01) |
| *A61Q 11/00* | (2006.01) |

(52) U.S. Cl.
CPC ............... *A61K 9/006* (2013.01); *A61K 8/19* (2013.01); *A61K 9/0036* (2013.01); *A61K 9/0043* (2013.01); *A61K 9/0046* (2013.01); *A61K 9/02* (2013.01); *A61K 33/34* (2013.01); *A61Q 11/00* (2013.01)

(58) Field of Classification Search
CPC ........ A61K 9/006; A61K 8/19; A61K 9/0036; A61K 9/0043; A61K 9/02; A61K 33/34; A61K 9/0046; A61Q 11/00
See application file for complete search history.

(56) References Cited

U.S. PATENT DOCUMENTS

| | | |
|---|---|---|
| 2,994,642 A | 8/1961 | Francois |
| 3,393,678 A | 7/1968 | Pacini |
| 3,803,308 A | 4/1974 | Zipper |
| 3,814,809 A | 6/1974 | Gordon |
| 3,930,834 A | 1/1976 | Schulteis et al. |
| 3,934,580 A | 1/1976 | Cournut |
| 4,039,406 A | 8/1977 | Stanley et al. |
| 4,136,172 A | 1/1979 | Walliczek |
| 4,242,192 A | 12/1980 | Dunning, Jr. et al. |
| 4,246,896 A | 1/1981 | Home, Jr. et al. |
| 4,294,894 A | 10/1981 | Vellucci |
| 4,332,791 A | 6/1982 | Raaf et al. |
| 4,391,270 A | 7/1983 | Uragami |
| 4,407,786 A | 10/1983 | Drake et al. |
| 4,457,909 A | 7/1984 | Tames |
| 4,618,489 A | 10/1986 | Pollock et al. |
| 4,642,230 A | 2/1987 | Whitehead et al. |
| 4,661,101 A | 4/1987 | Sustmann |
| 4,675,014 A | 6/1987 | Sustmann et al. |
| 4,680,309 A | 7/1987 | Maurer |
| 4,795,628 A | 1/1989 | Afseth |
| 4,959,216 A | 9/1990 | Daunter |
| 5,037,634 A | 8/1991 | Williams et al. |
| 5,063,065 A | 11/1991 | Bazterrica et al. |
| 5,164,367 A | 11/1992 | Pickart |
| 5,211,940 A | 5/1993 | Ishiguro et al. |
| 5,389,360 A | 2/1995 | Mobley et al. |
| 5,415,866 A | 5/1995 | Zook |
| 5,425,862 A | 6/1995 | Hartmann et al. |
| 5,456,602 A | 10/1995 | Sakuma |

(Continued)

FOREIGN PATENT DOCUMENTS

| | | |
|---|---|---|
| AU | 040296/72 | 9/1973 |
| CA | 2478137 A1 | 2/2006 |

(Continued)

OTHER PUBLICATIONS

US 11,052,109 B2, 07/2021, Abbott et al. (withdrawn)
F.M. Al-Kharafi*, B.G. Ateya and R.M. Abd Allah. Selective dissolution of brass in saltwater. Journal of Applied Electrochemistry 34: 47-53, 2004. (Year: 2004).*
Google_patent_search_6-25-21_mouthwash_dead_sea_salt_and_acetate_buffer (Year: 2021).*
Google_search_6-25-21_dead_sea_salt_and_acetate_buffer_mouthwash (Year: 2021).*

(Continued)

*Primary Examiner* — Michael P Cohen
(74) *Attorney, Agent, or Firm* — Wilmer Cutler Pickering Hale and Dorr LLP

(57) ABSTRACT

Copper ion treatments and methods of treatment are provided to treat various body conditions affecting the oral, respiratory and/or otic areas of the body. The copper ion treatments contain copper ions which bring about local and systemic therapeutic effects as a result of contacting anatomical tissue of the oral cavity, the nasal passages or ear canal. The copper ion treatments and methods involve copper ion-containing solutions, copper ion toothpaste and copper ion mouthwash. The copper ion-containing solutions can be delivered to the oral cavity by spraying or swabbing, can be delivered to the nostrils as spray, drops, or by swabbing, and can be delivered to the ear canal as spray, drops, or by swabbing. The copper ion toothpaste is used for brushing the teeth, and the copper ion mouthwash is used for rinsing the mouth.

16 Claims, 5 Drawing Sheets

(56) References Cited

U.S. PATENT DOCUMENTS

| | | | |
|---|---|---|---|
| 5,458,746 A | 10/1995 | Burgess et al. |
| 5,631,017 A | 5/1997 | Sharpe et al. |
| 5,798,116 A | 8/1998 | Brown |
| 5,981,475 A | 11/1999 | Reynolds |
| 6,022,545 A | 2/2000 | Schmittmann et al. |
| 6,042,848 A | 3/2000 | Lawyer et al. |
| 6,087,549 A | 7/2000 | Flick |
| 6,123,925 A | 9/2000 | Barry et al. |
| 6,153,210 A | 11/2000 | Roberts et al. |
| 6,231,889 B1 | 5/2001 | Richardson et al. |
| 6,294,186 B1 | 9/2001 | Beerse et al. |
| 6,296,881 B1 | 10/2001 | Hata et al. |
| 6,319,391 B1 | 11/2001 | Holderness et al. |
| 6,383,352 B1 | 5/2002 | Shyu et al. |
| 7,005,556 B1 | 2/2006 | Becker et al. |
| 7,087,249 B2 | 8/2006 | Burrell et al. |
| 7,252,839 B2 | 8/2007 | Hallinen et al. |
| 7,604,819 B2 | 10/2009 | Huey et al. |
| 7,776,915 B2 | 8/2010 | Morariu |
| 7,857,961 B2 | 12/2010 | Hayashi et al. |
| 8,118,028 B2 | 2/2012 | Karpati |
| 8,135,466 B2 | 3/2012 | Fuller et al. |
| 8,182,800 B2 | 5/2012 | MacDonald |
| 10,398,733 B2 | 9/2019 | Abbott et al. |
| 11,000,545 B2 | 5/2021 | Abbott et al. |
| 11,007,143 B2 * | 5/2021 | Abbott ............... A61K 9/006 |
| 11,083,750 B2 | 8/2021 | Abbott et al. |
| 2002/0114767 A1 | 8/2002 | Rolla |
| 2002/0136758 A1 | 9/2002 | Jehan |
| 2003/0099718 A1 | 5/2003 | Burrell et al. |
| 2003/0163149 A1 | 8/2003 | Heisinger |
| 2003/0166510 A1 | 9/2003 | Pickart |
| 2004/0171519 A1 | 9/2004 | DiSpirito et al. |
| 2004/0254097 A1 | 12/2004 | Patt |
| 2005/0048007 A1 | 3/2005 | Ruggles |
| 2005/0123620 A1 | 6/2005 | Chiou |
| 2005/0169852 A1 | 8/2005 | Roberge et al. |
| 2006/0122095 A1 | 6/2006 | Pelvin et al. |
| 2006/0216258 A1 | 9/2006 | Singleton et al. |
| 2006/0222622 A1 | 10/2006 | Faure |
| 2006/0253078 A1 | 11/2006 | Wu et al. |
| 2007/0014839 A1 | 1/2007 | Bracht |
| 2007/0053849 A1 | 3/2007 | Poyle et al. |
| 2007/0167971 A1 | 7/2007 | Huey et al. |
| 2007/0187327 A1 | 8/2007 | George et al. |
| 2007/0190175 A1 | 8/2007 | Cummins et al. |
| 2007/0243263 A1 | 10/2007 | Trogolo |
| 2007/0275021 A1 | 11/2007 | Lee et al. |
| 2007/0275073 A1 | 11/2007 | Huey et al. |
| 2007/0276308 A1 | 11/2007 | Huey et al. |
| 2008/0029915 A1 | 2/2008 | Waldron |
| 2008/0032119 A1 | 2/2008 | Feldhahn et al. |
| 2008/0081077 A1 | 4/2008 | Faryniarz et al. |
| 2008/0125686 A1 | 5/2008 | Lo |
| 2008/0195033 A1 | 8/2008 | Eagleson et al. |
| 2008/0274065 A1 | 11/2008 | Robinson et al. |
| 2008/0286212 A1 | 11/2008 | Cooley |
| 2008/0295843 A1 | 12/2008 | Haas |
| 2008/0299155 A1 | 12/2008 | McCook et al. |
| 2008/0311165 A1 | 12/2008 | Gabbay |
| 2008/0311218 A1 | 12/2008 | Oronsky et al. |
| 2008/0317836 A1 | 12/2008 | Dorogi et al. |
| 2009/0004294 A1 | 1/2009 | Margulies et al. |
| 2009/0018213 A1 | 1/2009 | Snyder et al. |
| 2009/0148540 A1 | 6/2009 | Martin et al. |
| 2009/0186071 A1 | 7/2009 | Huey et al. |
| 2009/0246292 A1 | 10/2009 | Seville et al. |
| 2009/0287131 A1 | 11/2009 | Neron et al. |
| 2009/0304813 A1 | 12/2009 | Hickok |
| 2009/0311305 A1 | 12/2009 | Abbott et al. |
| 2010/0003198 A1 | 1/2010 | Stolmeier et al. |
| 2010/0015898 A1 | 1/2010 | An et al. |
| 2010/0055138 A1 | 3/2010 | Margulies et al. |
| 2010/0068161 A1 | 3/2010 | Todary Michael |
| 2010/0068297 A1 | 3/2010 | Naughton |
| 2010/0100188 A1 | 4/2010 | Fuller et al. |
| 2010/0158989 A1 | 6/2010 | Mentkow et al. |
| 2010/0228174 A1 | 9/2010 | Huey et al. |
| 2010/0233248 A1 | 9/2010 | Huey et al. |
| 2010/0307503 A1 | 12/2010 | Iwamoto et al. |
| 2011/0064826 A1 | 3/2011 | Spurge |
| 2011/0086088 A1 | 4/2011 | Berry |
| 2011/0195108 A1 | 8/2011 | Fujimori et al. |
| 2012/0063262 A1 | 3/2012 | Imran |
| 2012/0071807 A1 | 3/2012 | McClure, Jr. |
| 2012/0071858 A1 | 3/2012 | Abbott et al. |
| 2012/0089068 A1 | 4/2012 | McClure, Jr. |
| 2013/0123716 A1 | 5/2013 | Abbott et al. |
| 2013/0226061 A1 | 8/2013 | Dickson |
| 2014/0221948 A1 | 8/2014 | Riesinger |
| 2014/0271495 A1 | 9/2014 | Abbott et al. |
| 2014/0271797 A1 | 9/2014 | Abbott et al. |
| 2014/0271798 A1 | 9/2014 | Abbott et al. |
| 2014/0271919 A1 | 9/2014 | Abbott et al. |
| 2016/0008272 A1 | 1/2016 | Abbott et al. |
| 2017/0000823 A1 | 1/2017 | Abbott et al. |
| 2017/0101699 A1 | 4/2017 | Moskovchenko et al. |
| 2018/0071206 A1 | 3/2018 | Abbott et al. |
| 2018/0133250 A1 | 5/2018 | Abbott et al. |
| 2019/0343876 A1 | 11/2019 | Abbott et al. |
| 2020/0206264 A1 | 7/2020 | Abbott et al. |
| 2020/0270723 A1 | 8/2020 | Abbott et al. |
| 2020/0281972 A1 | 9/2020 | Abbott et al. |
| 2021/0220397 A1 | 7/2021 | Abbott et al. |
| 2021/0220398 A1 | 7/2021 | Abbott et al. |
| 2021/0220399 A1 | 7/2021 | Abbott et al. |
| 2021/0228476 A1 | 7/2021 | Abbott et al. |

FOREIGN PATENT DOCUMENTS

| | | |
|---|---|---|
| CN | 101203232 A | 6/2008 |
| CN | 101534823 A | 9/2009 |
| EP | 0115130 B1 | 1/1987 |
| EP | 1236461 A1 | 9/2002 |
| EP | 3003046 B1 | 4/2016 |
| EP | 2762125 B1 | 8/2016 |
| FR | 2751544 A1 | 1/1998 |
| GB | 521215 A | 5/1940 |
| GB | 1333906 A | 10/1973 |
| GB | 1493750 A | 11/1977 |
| GB | 2449893 A | 12/2008 |
| JP | 2003212765 A | 7/2003 |
| RU | 2051154 C1 | 12/1995 |
| RU | 2155047 C1 | 8/2000 |
| SU | 1538101 | 1/1990 |
| WO | WO-9215329 A1 | 9/1992 |
| WO | WO-9958095 A2 | 11/1999 |
| WO | WO-2001026665 A1 | 4/2001 |
| WO | WO-0239963 A1 | 5/2002 |
| WO | WO-0241862 A1 | 5/2002 |
| WO | WO-02096202 A1 | 12/2002 |
| WO | WO-2004073758 A1 | 9/2004 |
| WO | WO-2005072691 A1 | 8/2005 |
| WO | WO-2006096937 A1 | 9/2006 |
| WO | WO-2008037262 A1 | 4/2008 |
| WO | WO-2009088270 | 7/2009 |
| WO | WO-2011069184 A1 | 6/2011 |
| WO | WO-201 2063262 A2 | 5/2012 |
| WO | WO-201 4151350 | 9/2014 |
| WO | WO-2018052995 | 3/2018 |
| WO | WO-2020171994 | 8/2020 |

OTHER PUBLICATIONS

Google_search_6-25-2021_copper_in_sea_salt (Year: 2021).*
"10 Homemade Gargles That Heal", Reader's Digest of Canada, www.readersdigest.ca/health/conditions/gaggle-gargles/, Jan. 4, 2008 (3 pages).
"Antimicrobial Copper FAQs", CDA Publication 201, Copper Development Association, Hemel Hempstead, United Kingdom, 2010 (8 pages).

(56) References Cited

OTHER PUBLICATIONS

"Assessment of the Safety and Efficacy of 3VM1001 Cream for Treatment of Chronic Pain Caused by Knee Osteoarthritis", ClinicalTrials.gov, https://clinicaltrials.gov/ct2/history/NCT02332148?V_3, dated Aug. 19, 2015 (6 pages).
"Buffer Reference Center", https://www.sigmaaldrich.com/life-science/core-bioreagents/biological-buffers/learning-center/buffer-reference-center.html, Oct. 26, 2008 (6 pages).
"Copper Sulfate", extract from Extoxnet: Extension Toxicology Network, <http://pmep.cce.cornell.edu/profiles/extoxnet/carbaryl-dicrotophos/copper-sulfate-ext.html>, May 1994 (2 pages).
"Copper Sulphate's Role in Agriculture", Excerpt from PAN Pesticides Database—Chemicals (1 page).
"Dangers of Copper Compounds (Sulfate, etc.)", Pubchem.ncbi.nlm.nih.gov/compound/Copper_sulfate#section=Top, 2007 (17 pages).
"Difference Between 304 vs 316 Stainless Steel", Eagle Stainless Tube & Fabrication, Inc., https://eagletube.com/about-us/news/304-vs-316-stainless-steel, Jun. 21, 2018 (2 pages).
"Lowering Infection Rates in Hospitals and Healthcare Facilities—The Role of Copper Alloys in Battling Infectious Organisms", Copper, BioHealth Partnership Publication, Edition 1, Mar. 2007, 26 pages.
"New Molecular Test Available to Diagnose Trichomonas Vaginalis in Asymptomatic and Symptomatic Females", PR Newswire, Oct. 18, 2012, 3 pages.
"Visual Analogue Scale", https://web.archive.org/web/20150804080655/https://www.physio-pedia.com/Visual_Analogue_Scale, Aug. 4, 2015, accessed Dec. 13, 2017 (6 pages).
"WOMAC Osteoarthritis Index," https://web.archive.org/web/20150907191904/https://www.physio-pedia.com/WOMAC_Osteoarthritis_Index, Sep. 7, 2015, accessed Dec. 13, 2017 (4 pages).
"Copper(II) Sulfate, Pentahydrate", ICSC 1416, CAS#: 7758-99-8, EC No. 231-847-6, International Labour Organization, World Health Organization, www.ilo.org/dyn/icsc/showcard.display?p_lang=en&p_card_id=1416&p_version=2, Oct. 2001 (2 pages).
EPA, "Drinking Water Criteria Document for Copper (Final Draft)", United States Environmental Protection Agency, EPA-600/X-84-190-1, pp. V-1-V-28, Mar. 1985 (38 pages).
Aaseth, J. et al., "Chapter 10: Copper (exceprt)", from Handbook on the Toxicology of Metals, Second Edition, vol. II: Specific Metals, Freiberg, et al., Eds., Elsevier Science Publishers B.V, Amsterdam, pp. 240-254,1986 (19 pages).
Amazon.com search for "Mouthwash", https://www.amazon.com/s/ref=sr_nr_n_0?fst=p90x%3A1%2Cas%3Aoff&rh=n%3A3760911%2Cn%3A10079992011%2Cn%3A3778161%2Ck%3Amouthwash&keywords=mouthwash&ie=UTF8&qid=1502940655&rnid=11055981, dated Aug. 16, 2017 (11 pages).
Anthoni, J.F., "The Chemical Composition of Sea Water", http://www.seafriends.org.nz/oceano/seawater.htm, accessed Jul. 28, 2016 (10 pages).
ASTM International, Designation: D1688-12, "Standard Test Methods for Copper in Water", dated 2012, accessed Oct. 24, 2018 (10 pages).
Azo Materials, "Medical Applications of Stainless Steel 304 (UNS S30400)", azom.com/Articles.aspx?=6641, Aug. 30, 2012 (3 pages).
Beigel, J.H. et al., "Remdesivir for the Treatment of Covid-19—Final Report", The New England Journal of Medicine, 383(19):1813-1826, published online Oct. 9, 2020 (14 pages).
Bhunya, et al., "Genotoxicity of an Inorganic Pesticide, Copper Sulphate in Mouse in vivo Test System", Cytologia, 52:801-808, 1987 (8 pages).
Blakley, B.R. "Overview of Copper Poisoning", Merck Manual: Veterinary Manual, https://www.merckvetmanual.com/toxicology/copper-poisoning/overview-of-copper-poisoning, 2018 (3 pages).
Blanc, C. et al., "Galvanic coupling between copper and aluminium in a thin-layer cell", Corrosion Science, 52(3):991-995, 2010 (6 Pages).
Borkow, G. et al., "Copper as a Biocidal Tool", Current Medicinal Chemistry, 12:2163-2175 (2005) (13 pages).

Cao, "Man Sperm Self Report", Harbin Publishing House, p. 27, Mar. 2012 (2 pages)—with English Translation.
CDA Research Group, Inc., "A Double-Blind, Placebo-Controlled, Crossover Study to Evaluate the Efficacy and Tolerability of 3VM1001 Cream for the Treatment of Pain Associated With Post-Herpetic Neuralgia: A Proof of Concept Study", Identifier NCT03421613, published on clinicaltrials.gov <URL: https://www.clinicaltrials.gov/ct2/show/NCT03421613>, published Jul. 10, 2018 (8 pages).
CDA Research Group, Inc., "A Double-blind, Placebo-controlled, Randomized Study to Assess the Safety and Efficacy of 3VM1001 Cream for the Treatment of Chronic Pain Caused by Osteoarthritis of the Knee: A Proof of Concept Study", Identifier: NCT02332148, Published on ClinicalTrials.Gov, <URL: https://clinicaltrials.gov/ct2/show/NCT02332148>, Published Aug. 21, 2015 (6 pages).
CDA Research Group, Inc., "A Double-Blind, Placebo-Controlled, Randomized Study to Evaluate the Safety and Efficacy of 3VM1001 Cream for the Treatment of Chronic Pain Caused by Osteoarthritis of the Knee: A Dose Ranging Study", Identifier: NCT03142178 published on clinicaltrials.gov <URL: https://www.clinicaltrials.gov/ct2/show/ NCT03142178 >, published Jul. 6, 2018 (9 pages).
CDA Research Group, Inc., "Assessment of the Safety and Efficacy of 3VM1001 Cream for Treatment of Chronic Pain Caused by Knee Osteoarthritis", U.S. National Library of Medicine, Clinical Trial NCT02332148, https://clinicaltrials.gov/ct2/show/NCT02332148, Aug. 21, 2015, accessed Dec. 12, 2017 (5 pages).
Centers for Disease Control, "CDC No Longer Recommends Oral Drug for Gonorrhea Treatment", Press Release, Aug. 9, 2012, 1 page.
Centers for Disease Control. "Pelvic Inflammatory Disease (PID)", CDC Fact Sheet, Dec. 12, 2012, 6 pages.
Chinese Office Action issued by the State Intellectual Property Office of People's Republic of China for Chinese Application No. 201480028588.X dated Oct. 13, 2017 (27 pages).
Collins, Reflections of Dentifrice Ingredients, Benefits and Recommendations: A Peer-Reviewed Publication, www.ineedce.com, accessed https://www.dentalacademyofce.com/courses/2086/pdf/1103cei_dentifrices_web.pdf, Oct. 2009 (11 pages).
Copper Gluconate, except from Wikipedia, https://en.wikipedia.org/wiki/Copper_gluconate, Mar. 29, 2017 (1 page).
Copper Glycinate Product Data Sheet, https://www.lookchem.com/Copper-glycinate/, dated 2008, accessed Aug. 30, 2018 (2 pages).
Database WPI, Week 199640, Thompson Scientific, London GB, An 1996-400647, XP002765918, 1996 (2 pages).
Database WPI, Week 200375, Thompson Scientific, AN 2003-793474, XP002767346, 2003 (2 pages).
De Rauglaudre, G. et al., "Tolerance of the association sucralfate / Cu—Zn salts in radiation dermatitis", Annales de dermatologie, 1:11-15 (2008)—English Abstract (5 pages).
Dispose—definition, https://www.merriam-webster.com/dictionary/dispose, downloaded Jun. 24, 2018 (1 page).
Dragani, R. "Does Salt Change the pH of Water?", https://sciencing.com/does-salt-change-ph-water-4577912.html., downloaded Dec. 31, 2019, Apr. 19, 2018 (3 pages).
Duguid, R., "Copper-inhibition of the growth of oral streptococci and actinomyces", Biomaterials, 4:225-227, Jul. 1983 (3 pages).
Edematous—Definition from The Medical Dictionary of the Free Dictionary Online, https://medical-dictionary.thefreedictionary.com/edematous, accessed Mar. 7, 2018 (7 pages).
European Extended Search Report issued in EP14767396.6, dated Feb. 9, 2017 (10 pages).
European Extended Search Report issued in EP14768757.8, dated Dec. 6, 2016 (9 pages).
European Extended Search Report issued in EP14768896.4, dated Feb. 27, 2017 (8 pages).
European Extended Search Report issued in EP20185469.2, dated Oct. 9, 2020 (10 pages).
European Extended Search Report issued in European Patent Application No. EP20161252.0, dated Jun. 17, 2020 (9 pages).
European Extended Search Report, issued in European Patent Application No. 17851454.3, dated Jul. 10, 2020 (14 pages).
European Partial Supplementary Search Report issued in EP17851454.3, dated Apr. 6, 2020 (15 pages).

(56) References Cited

OTHER PUBLICATIONS

Extended European Search Report issued in EP14767738.9, dated Jan. 2, 2017 (8 pages).
Faltermeier, R. B., "The Evaluation of Corrosion Inhibitors for Application to Copper and Copper Alloy Archaeological Artefacts", Thesis Submitted for the Degree of Doctor of Philosophy in the Faculty of Science of the University of London, Department of Conservation and Museum Studies, Institute of Archaeology, University College London, University of London, Jul. 1995 (332 pages).
Fenelon, A.M. et al., "The electrochemical synthesis of polypyrrole at a copper electrode: corrosion protection properties", Electrochimica Acta, 47:4467-4476, 2002 (10 pages).
Gerasimov, V. V. et al., "Effect of Temperature on the Rate of Corrosion of Metals", Russian Chemical Bulleting, pp. 1192-1197, Oct. 6, 1957 (6 pages).
Google Search "Copper Salt for Sore Throat 'CORONAVIRUS'", dated Aug. 24, 2020 (2 pages).
Gray, L.W. et al., "Urinary Copper Elevation in a Mouse Model of Wilson's Disease Is a Regulated Process to Specifically Decrease the Hepatic Copper Load", PLoS One, 7(6):e38327, Jun. 22, 2012 (11 pages).
Higdon, J. et al., "Copper", Linus Pauling Institute, Oregon State University, Apr. 2003, 8 pages.
International Search Report and Written Opinion issued by the U.S. Patent and Trademark Office as International Searching Authority, issued in International Application No. PCT/US2020/17454, dated Jun. 23, 2020 (12 pages).
International Search Report and Written Opinion issued by U.S. Patent and Trademark Office as International Searching Authority, in International Application No. PCT/US17/51356, dated Jan. 18, 2018 (11 pages).
Ion, Wikipedia, https://en.wikipedia.org/wiki/Ion, accessed Aug. 30, 2018 (11 pages).
Khaled, K.F., "Studies of the corrosion inhibition of copper in sodium chloride solutions using chemical and electrochemical measurements", Materials Chemistry and Physics, 125:427-433, 2011 (7 pages).
Kirkpatrick, K., "Does saltwater work as mouthwash?", http://health.howstuffworks.com/wellness/oral-care/products/saltwater-as-mouthwash.htm, available online Sep. 18, 2011, accessed Mar. 4, 2019 (6 pages).
Lindeburg, M.R., Chemical Engineering Reference Manual for the PE Exam, Seventh Edition, Professional Publications, Inc., Belmont, California, p. 20-10, 2013 (3 pages).
Malik, R. "Warm Saline Rinses", http://www.nature.com/articles/sj.bdj.2009.1093.pdf, accessed Dec. 31, 2019, Br. Dental J., 207(11):520, 2009 (2 page).
Maltz, M. et al., "Effect of copper fluoride and copper sulfate on dental plaque, Streptococcus mutans and caries in hamsters", Scand. J. Dent. Res., 96:390-392, Oct. 1, 1988 (3 pages).
Marques, M.R.C. et al., "Simulated Biological Fluids with Possible Application in Dissolution Testing", Dissolution Technologies, 18(3):15-28, Aug. 2011 (14 pages).
Metikoš-Hukovi?, M. et al., "Copper Corrosion at Various pH Values with and without the Inhibitor", Journal of Applied Electrochemistry, 30:617-624, 2000 (8 pages).
Michels, H.T. et al., "Copper Alloys for Human Infectious Disease Control", presented at Material Sciences and Technology Conference, Copper for the 21st Century Symposium, Pittsburgh, PA, Sep. 25-28, 2005, 11 pages.
Moore, R.L. et al., "Evaluating the Anti-Plaque Capabilities of a Copper-Containing Prophylaxis Paste", J. Periodontal., 60(2):78-80, Feb. 1989 (3 pages).
Mulligan, A.M. et al., "The effect of increasing copper content in phosphate-based glasses on biofilms of Streptococcus sanguis", Biomaterials, 24:1797-1807, 2003 (11 pages).
Nkonzo, N., "Antimicrobial Copper", International Copper Association, Copper Development Association, May 5, 2010, 6 pages.
Owen, D.H. et al., "A Vaginal Fluid Simulant", Contraception, 59(2):91-95, Feb. 1999 (5 pages).
Perrie, Y. et al., "Chapter 1: Controlling Drug Delivery", FASTtrack: Pharmaceutics—Drug Delivery and Targeting, Second Edition, Sample Chapter, 14, Jun. 2012 (26 pages).
Ramachandran, S. et al., "Gluconic Acid: Properties, Applications and Microbial Production", Food Technol. Biotechnol., 44(2):185-195, 2006 (11 pages).
Read, A.J., "Dissolution of Copper in Weakly Acidic Solutions", The Journal of Physical Chemistry, 76(24):3656-3663, 1972 (8 pages).
Robinson, J., "No improvement in mortality rates for COVID-19 patients treated with remdesivir", the Pharmaceutical Journal, DOI:10.1211/PJ.2020.20208045, published online Jun. 8, 2020 (3 pages).
Roldan, S, et al., "Biofilms and the tongue: therapeutical approaches for the control of halitosis", Clin. Oral Invest., 7:189-197, 2003 (9 pages).
Rosenhein, L.D., "The Household Chemistry of Cleaning Pennies", Applications and Analogies, Journal of Chemical Education, 78(4):513-515, Apr. 2001 (3 pages).
Sawyer, D.T., "Metal-Gluconate Complexes", Chem. Rev., 64(6):633-643, 1964 (11 pages).
Saxer, U P et al., "New Studies on Estimated and Actual Toothbrushing Times and Dentifrice Use", J. Clin. Dent., 9(2):49-51, 1998 (1 page)—Abstract Only.
Shackel, N.A. et al., "Copper-salicylate gel for pain relief in osteoarthritis: a randomised controlled trial", MJA, 167:134-136, Aug. 4, 1997 (3 pages).
Solioz, "Dry Copper Kills Bacteria on Contact", Science Daily, Feb. 22, 2011, 4 pages.
Stein, R., "Gonorrhea Evades Antibiotics, Leaving Only One Drug to Treat Disease", www.npr.org/blogs/health, Aug. 10, 2012, 5 pages.
Stokinger, H.E. et al., "Chapter 11: Copper", in Patty's Industrial Hygiene and Toxicology: vol. 2A—Toxicology, Clayton et al., Eds., John Wiley Sons, New York, pp. 1620-1630, 1981 (16 pages).
Tamba, B.I. et al., "Common Trace Elements Alleviate Pain in an Experimental Mouse Model", Journal of Neuroscience Research, 91:554-561, 2013 (8 pages).
VersaBase Cream, Product Information Document, from PCCA, https://pccarx.com/Products/ProductCatalog?pid=30-3641, accessed Dec. 31, 2019 (4 pages).
Wang, et al., "Family Planning Technology", Shanghai Science and Technology Press, p. 334, Dec. 31, 1997 (2 pages)—English Excerpt.
Wikipedia, "Acetic acid", https://en.wikipedia.org/wiki/Acetic_acid, accessed Oct. 14, 2019 (19 pages).
Wikipedia, "Buffer Solution", Wikipedia, the Free Encyclopedia, https://en.wikipedia.org/wiki/Buffer_Solution, accessed Apr. 7, 2017 (8 pages).
Wikipedia, "Copper(I) chloride", https://en.wikipedia.org/wiki/Copper(I)_chloride, accessed Oct. 13, 2019 (8 pages).
Wikipedia, "Salt (chemistry)", https://en.wikipedia.org/wiki/Salt_(chemistry), accessed Oct. 14, 2019 (6 pages).
Wikipedia, "Suspension (chemistry)", https://en.wikipedia.org/wiki/Suspension_(chemistry), accessed Oct. 13, 2019 (3 pages).
Yassin, N. et al., "Effect of a topical copper indomethacin gel on inflammatory parameters in a rat model of osteoarthritis", Drug Design, Development and Therapy, 9:1491-1498, 2015 (8 pages).
Zatcoff, R.C. et al., "Treatment of tinea pedis with socks containing copper-oxide impregnated fibers", The Foot, 18:136-141 (2008) (6 pages).
Zwirner, E., "5 Advantages of Vertical Storage Tanks", https://www.zwirnerequipment.com/blog/5-advantages-vertical-storage-tanks/, Oct. 20, 2014 (2 pages).
"About the Study: Elvis COVID-19 Study Full Information", The University of Edinburgh, URL <https://www.ed.ac.uk/usher/elvis-covid-19/about-the-study>, published Jun. 24, 2020 (4 pages).
Al-Kharafi, et al., "Selective dissolution of brass in salt water", Journal of Applied Electrochemistry, 34:47-53, 2004 (7 pages).
Bauer, "Understanding radiation dermatitis", American Nurse Today, 11(1):13-15, Jan. 2016 (3 pages).

(56) References Cited

OTHER PUBLICATIONS

Bauer, "Understanding radiation dermatitis", URL<http://old.woundcareadvisor.com/understanding-radiation-dermatitis/>, Wound Care Advisor, vol. 5, No. 3, May/Jun. 2016 (6 pages).
Ben-Hur, et al., "Phosphorus Burns: The Antidote: A New Approach", British Journal of Plastic Surgery, 25:245-249, 1972 (5 pages).
Bianchetti, M. G., et al., "Body fluids and salt metabolism—Part I", Italian Journal of Pediatrics, 35:36, Nov. 19, 2009 (6 pages).
Biocompatible, definition from Cambridge Dictionary, URL <https://dictionary.cambridge.org/us/dictionary/english/biocompatible>, accessed Oct. 26, 2020 (6 pages).
Cancer Facts & Figures 2016, American Cancer Society, URL <https://www.cancer.org/research/cancer-facts-statistics/all-cancer-facts-figures/cancer-facts-figures-2016.html>, 2016 (72 pages).
Cortes, et al., "The use of copper to help prevent transmission of SARS-coronavirus and influenza viruses. A general review", Diagnostic Microbiology and Infectious Disease, 98:115176, available online Aug. 15, 2020 (5 pages).
Google Search, "copper in sea salt", URL <https://www.google.com/search?q=copper+in+sea+salt&ei=TRrWYJyaCemr5NoPvlmPIA . . . >, accessed Jun. 25, 2021 (2 pages).
Google Search, "Copper phosphate buffered saline", URL: <https://scholar.google.com/scholar?hl=en&as_sdt=0%2C47&q=copper+phosphate+buffered . . . >, accessed Aug. 5, 2021 (2 pages).
Google Search, "dead sea salt and acetate buffer mouthwash", URL <https://www.google.com/search?q=dead+sea+salt+and+acetate+buffer+mouthwash&ei=d . . . >, accessed Jun. 25, 2021 (2 pages).
Google Search, "mouthwash dead sea salt and acetate buffer", URL <https://google.com/search?q=mouthwash+dead+sea+salt+and+acetate+buffer&tbm=. . . >, accessed Jun. 25, 2021 (2 pages).
International Search Report and Written Opinion issued by the U.S. Patent and Trademark Office as International Searching Authority, in International Application No. PCT/US21/24555, dated Jul. 8, 2021 (9 pages).
Iqbal, K et al., "Role of Different Ingredients of Tooth Pastes and Mouthwashes in Oral Health", Journal of the Pakistan Dental Association, 20(03): 163-170, Jul.-Sep. 2011 (8 pages).
Pramanik, et al., "A novel study of antibacterial activity of copper iodide nanoparticle mediated by DNA and membrane damage", Colloids and Surfaces B: Biointerfaces, 96:50-55, published online Apr. 5, 2012 (6 pages).
Wikipedia, "Saline (Medicine)", URL <https://en.wikipedia.org/wiki/Saline_(medicine)>, accessed Jul. 21, 2021 (9 pages).
Wong, R. K. S. et al., "Clinical practice guidelines for the prevention and treatment of acute and late radiation reactions from the MASCC Skin Toxicity Study Group", Support Care Cancer, DOI 10.1007/S00520-013-1896-2, published online Aug. 14, 2013 (16 pages).

* cited by examiner

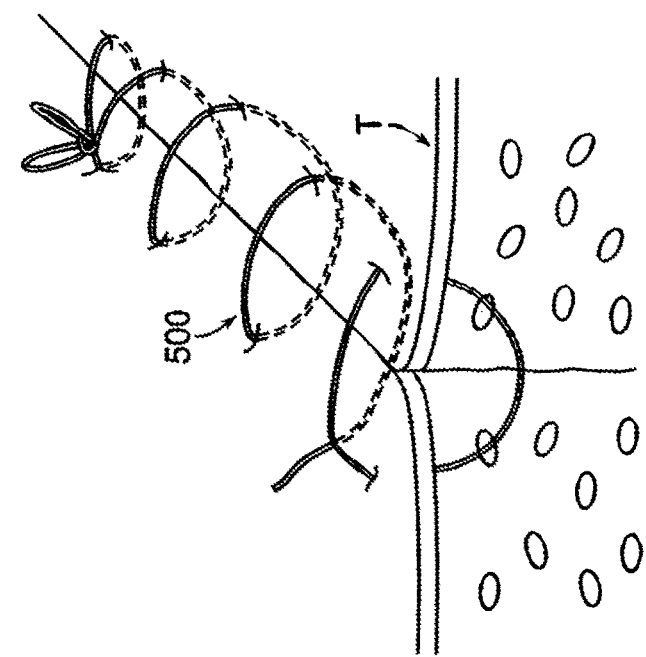
FIG. 19
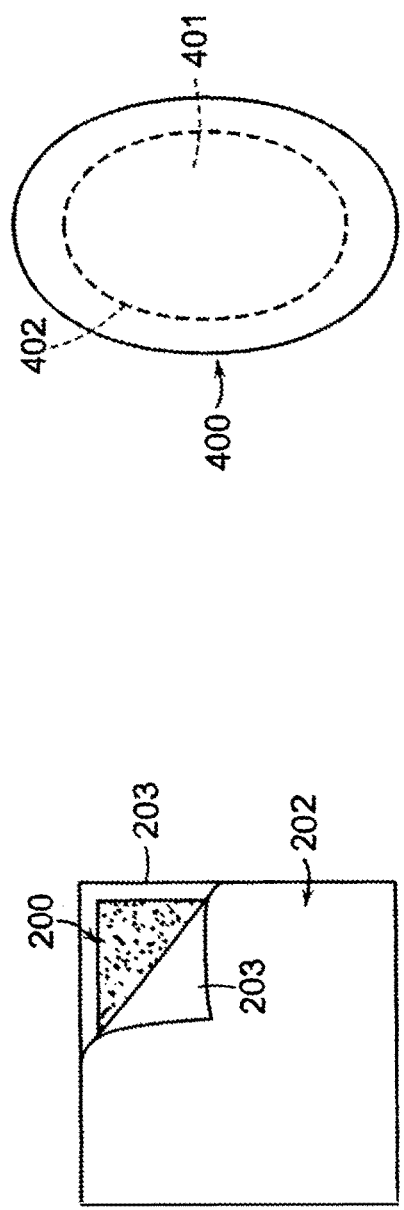
FIG. 18
FIG. 16
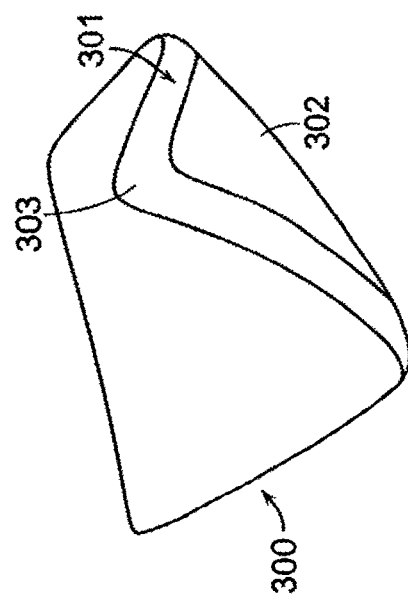
FIG. 17

TOPICAL COPPER ION TREATMENTS AND METHODS OF TREATMENT USING TOPICAL COPPER ION TREATMENTS IN THE ORAL-RESPIRATORY-OTIC AREAS OF THE BODY

CROSS-REFERENCE TO RELATED APPLICATIONS

This application is a continuation of U.S. patent application Ser. No. 13/842,310, filed Mar. 15, 2013. The entire contents of which are hereby incorporated by reference in their entirety.

BACKGROUND OF THE INVENTION

Field of the Invention

The invention pertains generally to topical treatments containing copper ions and to methods of treating body conditions using topical treatments containing copper ions in various anatomical areas of the body. More particularly, the invention pertains to treating body conditions affecting the oral, respiratory and/or otic areas using topical treatments containing copper ions.

Brief Discussion of the Related Art

Many various abnormal body conditions are caused by harmful pathogens or microbes, examples of which include bacteria, fungi and viruses. Abnormal body conditions that arise in or affect the genital area in women typically affect the vagina and are commonly referred to as "vaginitis". The term "vaginitis" encompasses infection and/or inflammation of the vagina caused by bacteria, fungi and/or viruses. Vaginitis may extend to the external female genital area, i.e. the vulva, in which case it is usually referred to as "vulvovaginitis". In addition, bacterial, fungal and viral conditions that affect all or part of the genital area in women, i.e. vagina, vulva and/or surrounding anatomical area, may also affect all or part of the rectal (anal) area, i.e. the rectum (anal canal) and surrounding anatomical area. In men, infection and/or inflammation of bacterial, fungal and/or viral origins may affect all or part of the rectal area and also a or part of the genital area, i.e. the penis, scrotum and surrounding anatomical area.

Vaginitis that is bacterial in origin is commonly called "bacterial vaginosis". Many different bacteria are responsible for bacterial vaginosis and some of these bacteria are the cause of sexually transmitted diseases in women and men. Examples of sexually transmitted bacterial diseases that affect the vagina and surrounding anatomical areas are gonorrhea and chlamydia, which appear in the general population on a widespread basis. It is estimated by the Centers for Disease Control and Prevention (CDC) that more than 700,000 people annually in the U.S. alone acquire new gonorrhea infections. According to the CDC, over 1.3 million chlamydia infections were recorded in the U.S. in 2010 alone. In addition, there are a large number of undiagnosed, untreated or unreported infections of gonorrhea and chlamydia because the diseases may be asymptomatic or present with only very mild symptoms. Oftentimes, gonorrhea and chlamydia occur together. Gonorrhea and chlamydia may also appear in the mouth, throat and rectum (anus) in men and women. If left untreated, gonorrhea and chlamydia can spread to the uterus and/or Fallopian tubes and may cause pelvic inflammatory disease (PID), infertility, ectopic pregnancies, chronic pelvic pain and increased risk for infection with the human immunodeficiency virus (HIV). Untreated gonorrhea may also affect the blood, joints and heart valves. The usual treatments for gonorrhea and chlamydia are appropriate antibiotics, but history has demonstrated that over time many bacterial diseases develop a resistance to antibiotics. Indeed, according to the CDC, numerous antibiotics previously used to treat gonorrhea have lost their effectiveness, and there is currently only one remaining drug, i.e. the injectable antibiotic ceftriaxone, proven effective for treating gonorrhea. There is great concern in the medical community that it is only a matter of time before gonorrhea becomes resistant to this last remaining drug. Other types of pathogens and microbes, such as the bacteria *streptococcus* and *staphylococcus* and the parasitic protozoan trichomonas, may also affect the vagina and surrounding anatomical areas resulting in abnormal biological conditions. As with gonorrhea, *staphylococcus* infections are especially problematic because certain strains of the bacteria have become antibiotic resistant. Infections in the vagina may spread to the uterus, resulting in PID which is often a very painful and serious condition with potentially harmful and permanent complications.

In addition to being susceptible to abnormal body conditions caused by bacteria, the vagina and surrounding anatomical areas are susceptible to various abnormal body conditions caused by viruses and fungi. Viral diseases that arise in or affect the vagina and surrounding anatomical areas include herpes (Types I and II), human papilloma virus (HPV) and HIV, all of which are sexually transmittable. Herpes, HPV and HIV can also be found in the areas of the mouth, skin and rectum (anus). Fungal diseases that arise in or affect the vagina include yeast infections, particularly candida, and thrush. Fungi are also responsible for abnormal biological conditions in other areas of the body such as the mouth (thrush), feet, skin and nails. There is no cure for herpes and HIV. Anti-viral drugs are available to alleviate herpes symptoms and suppress the herpes virus so that active infections recur less frequently and are of shorter duration, but these drugs are associated with significant side effects. Infection with HPV is usually treated with topical medications, oral medications and/or surgical removal of warts. Complications of HPV infection include increased risk for cervical, rectal and vulvar cancers. Available treatments for HIV are designed to suppress the virus and boost the immune system in hope of avoiding opportunistic infections and delaying or preventing the onset of full-blown acquired immune deficiency syndrome (AIDS). In recent years, it was hoped that a vaginal microbicide gel called PRO 2000 would be effective at reducing HIV infection when used shortly before sexual intercourse, but unfortunately the compound was found to be ineffective in a large scale clinical trial. Topical and oral medications are available to treat yeast and other fungal infections, but are limited in effectiveness such that fungal infections are often not eradicated and thus reoccur. The vast majority of abnormal body conditions caused by bacteria, viruses and fungi that affect the genital and/or rectal areas in women also affect the genital and/or rectal areas in men.

In addition to conditions caused by harmful pathogens or microbes, hemorrhoids are another abnormal body condition that affects the rectum (anus) in men and women and may cause rectal pain, swelling, discomfort and/or itching. Conventional treatments for hemorrhoids include topical medications and surgery. In addition to harmful microbes and pathogens, sperm are microbes that appear in the vagina after intercourse. Numerous spermicidal contraceptive compounds are available for introduction in the vagina. Typically, these must be introduced in the vagina very shortly before intercourse and are therefore oftentimes inconvenient. When intercourse takes place without contraception and there is concern for an unwanted pregnancy, drugs known as the "morning after par or -emergency contraceptives" are sometimes prescribed to prevent pregnancy, but these drugs are not 100% effective and may have undesirable side effects.

Abnormal body conditions of bacterial, viral and fungal origins commonly arise in dermatological areas of the body, i.e. skin and nails. The skin and soft tissue are common sites for infections caused by various bacteria including *staphylococcus, enterobacter, pseudomonas,* and *streptococcus.* Oftentimes, infections develop on the skin at the site of a cut scratch, abrasion, burn, splinter, boil, pimple, blister, insect bite or other wound or trauma that damages or breaks the skin or provides a point of entry for bacteria and/or other harmful organisms. Viruses such as herpes, shingles and HPV are also the cause of abnormal body conditions on the skin. In particular, herpes causes cold sores (fever blisters), shingles causes painful eruptions, and HPV causes warts on the skin. Other organisms also cause warts on the skin. The skin is susceptible to various fungal conditions, such as "athlete's foot" which commonly occurs on the feet and rashes such as ringworm. Infections of the nails, particularly fungal infections of the toenails, are also a common and tenacious problem. The skin is further susceptible to various body conditions resulting from aging, environmental factors and various external and internal causes, such conditions including sun/wind damage, dry skin, age spots, pigmentation, scaring, blisters, boils, cysts, pimples, cuts, scratches, burns, abrasions, splinters, insect bites and stings, animal bites and scratches, ulcers, loss of elasticity or collagen that manifests as wrinkles and sagging skin, acne, and many types of rashes, such as measles, chicken pox, eczema, psoriasis, impetigo and rosacea, due to various underlying external and internal causes. Various topical and oral prescription and non-prescription medications and products are available to treat the foregoing skin conditions. The skin is also a carrier for bacteria, viruses and fungi, seeing as how the skin regularly comes in contact with a plethora of pathogens and microbes. Consequently, many products such as sanitizing hand and body lotions and wipes are available commercially for the purpose of reducing germs on the skin.

The oral-respiratory-otic areas of the body, i.e. mouth, throat, nose, sinuses and ears are also common sites for abnormal body conditions due to the aforementioned pathogens and microbes. In addition, various allergies cause undesirable body conditions that impact the oral-respiratory-otic areas of the body, particularly the throat, nose and sinuses. Asthma is a chronic inflammatory disease of the airways responsible for undesirable conditions. Bacteria, viruses, fungi, allergies and/or asthma are responsible for many unwanted symptoms that appear in the oral-respiratory otic areas of the body including sore throat, tonsillitis, colds, bronchitis, sinusitis, rhinosinusitis, wheezing, ear infections, earache, pressure in the ears, cold sores, mouth ulcers, canker sores, cough, hoarseness or laryngitis, congestion, runny nose, sneezing, sore gums, periodontal disease, tooth decay and halitosis (bad breath). A vast array of prescription and non-prescription drugs and products are commercially available to treat oral-respiratory-otic conditions.

The prescription drugs and even many of the non-prescription drugs or products used to treat the numerous body conditions described above have many drawbacks including undesirable or potentially harmful side effects, high risk of harm in the event of overdose or improper use, high cost, limited effectiveness, the need for close medical monitoring, and inconvenience. Moreover, there is presently no single compound or product to treat a wide range of body conditions affecting the genital-rectal areas that include the vagina, rectum (anus), and surrounding anatomical areas, the oral-respiratory-otic areas that include the mouth, throat, airway, nose, sinuses and ears, and the dermatological areas that include the skin and nails, much less a non-pharmaceutical topical treatment that is safe, cost-effective, easy and convenient to use, and capable of being embodied in different forms depending on the intended anatomical area or areas of use.

It has previously been established that copper possesses properties by which it is capable of killing, neutralizing and preventing the growth of human pathogens. It is known that many bacteria identified as human pathogens cannot survive on surfaces of copper metal. U.S. Pat. No. 8,135,466 B2 to Fuller et al discloses a joint prosthesis having an implant body with an external surface containing an antimicrobial metal where the antimicrobial metal may be copper. U.S. Patent Application Publications No. US 2012/0071807 A1 and No. US 2012/0089068 A1 to McClure, Jr. disclose wound dressings containing a metal-based antimicrobial agent where the metal-based antimicrobial agent may be a mixture of silver ions and copper Ions. Devices having an external surface of copper metal for insertion in the vagina to treat abnormal biological conditions have been proposed by Applicants in U.S. patent application Ser. No. 12/157,823 filed Jun. 13, 2008 (abandoned), Ser. No. 13/317,230 filed Oct. 12, 2011, and Ser. No. 13/484,005 filed May 4, 2012, the entire disclosures of which are incorporated herein by reference.

Topical substances containing particles of copper or its alloys have been proposed for health support uses. A product called "MesoCopper®" sold by Purist Colloids, Inc. is a colloidal copper solution containing nano particles of copper for use on the skin to minimize the appearance of fine lines and wrinkles. Another version of the product is sold as an ingestible mineral supplement. Copper peptides for use on the skin are also commercially available and these require peptides, i.e. small fragments of protein that have an affinity for copper to which they bind very tightly. U.S. Pat. No. 7,776,915 B2 to Morariu discloses a topical composition containing, at a minimum, a lipoic acid, a carnitine and a carnosine, where the carnosine may be chelated to zinc or copper ions. The intended use for the topical composition is to improve the appearance of aged skin. U.S. Patent Application Publication No. US2008/0195033 A1 to Eagleson et al discloses use of a metal substance to treat diseases in the body. The metal substance is primarily a colloidal suspension and delivery of the substance to the body may require the use of electricity. Prior to the present invention, it has not been recognized to provide a simple solution containing copper ions for use as a topical treatment to be applied directly to anatomical tissue to treat body conditions and/or for use in conjunction with various carriers including creams, gels, lotions, foams, pastes, other solutions, suppositories, tampons, body wipes, wound dressings, skin patches and suture material to form topical treatments in which the carriers facilitate delivery of the copper ions to contact anatomical tissue depending on the anatomical area or areas of use on the body.

SUMMARY OF THE INVENTION

An aspect of the invention pertains to a copper ion treatment and to methods for treating conditions affecting the oral cavity where the copper ion treatment is a copper ion toothpaste composed of a toothpaste base material and a copper ion-containing solution mixed with the toothpaste base material. The copper ion-containing solution is composed of a biocompatible solution and copper ions contained in the biocompatible solution. When the copper ion toothpaste is used to brush the teeth, the copper ions contact the teeth and mix with saliva within the oral cavity, thereby providing therapeutic effects. A method of treatment carried out using the copper ion toothpaste is particularly advantageous for treating conditions including one or more of halitosis, sore gums, inflamed gums, gum infections, periodontal disease and tooth decay, brings about local and systemic therapeutic effects. Another aspect of the invention pertains to a copper ion treatment and to methods for treating conditions affecting the oral cavity where the copper ion treatment is a copper ion mouthwash composed of a mouthwash base solution and the copper ion-containing solution mixed with the mouthwash base solution. In a method of treatment carried out using the copper ion mouthwash to gargle or rinse the mouth, the copper ions provide therapeutic effects like those provided by the copper ion toothpaste.

A further aspect of the invention involves treating conditions affecting the oral cavity by spraying a copper ion-containing solution inside the mouth such that the copper ions contact anatomical tissue inside the mouth and provide local and systemic therapeutic effects. Depending on the condition or conditions being treated, the copper ion-containing solution can be sprayed into the throat, onto a canker sore, mouth sore or mouth ulcer, onto areas of the gums that are sore, inflamed or infected, on the tongue and/or on the inside of the cheeks. The copper ion-containing solution could also be delivered to areas of the oral cavity by swabbing the areas with the solution. The conditions treated by spraying the copper ion-containing solution inside the mouth may include one or more of colds, sore throat, bronchitis, cough, mouth sores, canker sores, mouth ulcers, allergies, tonsillitis, periodontal disease, hoarseness, laryngitis, halitosis, *streptococcus, staphylococcus, trichomonas*, fungal disease, thrush, herpes (I and II), HIV, HPV, chlamydia, gonorrhea, sore gums, infected gums, and inflamed gums.

It is also an aspect of the invention to provide a method of treating conditions affecting the respiratory area of the body by delivering into the nostrils a copper ion-containing solution. The copper ion-containing solution can be delivered into the nostrils by spray, by drops or by swabbing with the copper ion-containing solution. The method can be used to treat conditions affecting the respiratory areas including one or more of colds, congestion, nasal discharge, runny nose, allergies, asthma, wheezing, sinusitis, rhinosinusitis, sinus pressure and sneezing.

An additional aspect of the invention involves treating conditions affecting the otic area by delivering a copper ion-containing solution into the ear canal of one or both ears. The copper ion-containing solution can be delivered into the ear canals in the form of a spray or drops, or by swabbing with the copper ion-containing solution. The method is particularly advantageous to treat conditions including one or more of earache, ear infection, stuffy ears and pressure in the ear.

BRIEF DESCRIPTION OF THE DRAWINGS

FIG. 16 is a font view of a package containing a body wipe carrying a copper ion treatment and showing the package partially open to remove the body wipe therefrom.

FIG. 17 is a perspective view of a wound dressing suppled with a copper ion treatment.

FIG. 18 is a plan view of a skin patch carrying a copper ion treatment.

FIG. 19 is a perspective view of sutures created in anatomical tissue using suture material carrying a copper ion treatment.

DETAILED DESCRIPTION OF THE INVENTION

Figure 3:
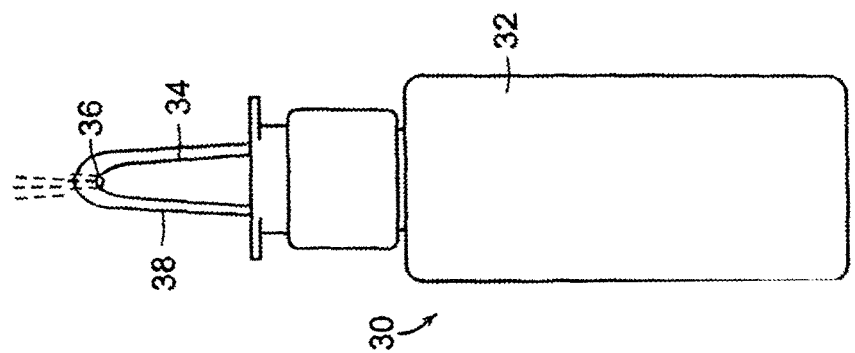
FIG. 3 is a side view of a bottle containing a copper ion treatment wherein the bottle is squeezable to dispense the copper ion treatment from a dropper on the bottle.

A solution containing copper ions, i.e. copper ion-containing solution, for use as a topical treatment containing copper ions, i.e. topical copper ion treatment, to treat body conditions is produced according to a process or method by which copper ions from copper metal are leached into an appropriate biocompatible solution. As used herein, "copper metal" means pure copper (99.5% or greater copper after processing) and copper alloys such as brasses, bronzes, copper-nickels and copper-nickel-zincs. Preferably, pure copper is used as the copper metal. Example 1 describes the steps involved in producing an amount of copper ion-containing solution equal or substantially equal to 7.44 ounces.

Example 1

7.44 ounces of biocompatible saline solution buffered with acetic acid and sodium acetate to a pH of 5 (±0.4) is placed in a container or vessel with a tight, removable lid to minimize evaporation. The container is placed in an incubator or oven at a temperature of 37° Celsius (±1° C.). When the saline solution has reached 37° Celsius, 102 grams of pure copper metal in solid form is placed in the heated solution within the container, and the container with the tight lid thereon is placed in the incubator at 37° Celsius for 24 hours. During the 24 hour period, copper ions from the copper metal leach into the solution. At the end of the 24 hour period, the container is removed from the incubator and the copper metal is removed or separated from the solution. The amount of solution remaining after removal or separation of the copper metal therefrom constitutes the copper ion-containing solution and should be essentially 7.44 ounces with minimal evaporation. The copper ion-containing solution produced according to this process contains copper ions in an amount equal or substantially equal to 46 milligrams when analyzed for copper content by inductively coupled plasma/optical emission spectroscopy (ICP/OES). The copper ion-containing solution is stored at room temperature and is ready for use in this form as a topical copper ion treatment to be applied to anatomical tissue to treat body conditions. In addition, the copper ion-containing solution is ready for use in conjunction with various carriers including creams, gels, lotions, foams, pastes, other solutions, suppositories, tampons, body wipes, wound dressings, skin patches and suture material to form topical copper ion treatments in which the carriers facilitate delivery of the copper ion treatments to contact anatomical tissue to treat body conditions.

The solid pure copper metal in Example 1 may be in the form of one or more sheets of pure copper metal, typically in the range of 0.03 to 0.06 inch thick, of appropriate length and width to provide the 102 grams of pure copper metal. In practice, the process described in Example 1 has been carried out using as the copper metal four vaginal therapeutic devices made of pure copper in accordance with Applicants' prior patent application Ser. No. 13/464,005 previously incorporated herein by reference in its entirety. In this case, each vaginal therapeutic device used was 3.25 inches long by 0.750 inch wide with a wall thickness of 0.031 inch providing 26.5 grams of pure copper. The biocompatible saline solution used in the process described in Example 1 is commercially available from B. Braun Medical. As an alternative to the biocompatible saline, vaginal simulating fluid (VSF) buffered with acetic acid to a pH of 5 (±0.4) can be used as the biocompatible solution, but will produce less leaching of copper ions from copper metal over the 24 hour period. The VSF can be prepared in accordance with published literature, e.g. Owen, D. H., Katz, D. F., "A Vaginal Fluid Simulant", Contraception, pages 91-05 (1999). The process described in Example 1 can be modified to eliminate the step of heating the solution prior to placement of the copper metal therein. In the latter case, the copper metal and unheated solution are placed in the container, the container with the tight lid thereon is placed in the incubator at 37° Celsius and, once the solution has reached 37° Celsius, the container with the heated solution and copper metal therein is allowed to remain in the oven for 24 hours. The copper metal can be removed or separated from the solution in various ways, such as by lifting the metal out of the solution or pouring the solution alone into another container. Of course, the quantities of biocompatible saline and solid copper mental used in Example 1 can be proportionately increased to produce a greater amount of copper ion-containing solution with each process.

The copper ion-containing solution is believed to have the greatest effectiveness for treating a wide range of body conditions when the solution contains the amount of copper ions leached into the saline from the copper metal over a 24 hour period as described in Example 1. However, it should be appreciated that the process described in Example 1 can be modified to obtain lower copper ion concentrations by adjusting the length of time that the container containing the heated saline and copper metal is allowed to remain in the incubator or oven as explained below in Examples 2, 3 and 4.

Example 2

Follow the steps of Example 1 but allow the container containing the saline and copper metal to remain in the oven at 37° C. for one hour to obtain a copper ion-containing solution that contains an amount of copper ions equal or substantially equal to 8.8 mg.

Example 3

Follow the steps of Example 1 but allow the container containing the saline and copper metal to remain in the oven at 37° C. for eight hours to obtain a copper ion-containing solution that contains an amount of copper ions equal or substantially equal to 22 mg.

Example 4

Follow the steps of Example 1 but allow the container containing the saline and copper metal to remain in the oven at 37° C. for 72 hours to obtain a copper ion-containing solution that contains an amount of copper ions equal or substantially equal to 35 mg.

The copper ion-containing solution in its original form, i.e. at the end of the processes of Examples 1-4, can be applied directly to anatomical tissue in various anatomical areas of the body as a copper ion treatment to treat various body conditions. Many types of containers or bottles can be used to hold a quantity of the copper ion-containing solution and to dispense or apply the copper ion-containing solution to anatomical tissue in accordance with the intended anatomical area or areas of use. The copper ion-containing solution may also be used in conjunction with various carriers including creams, lotions, gels, foams, pastes, other solutions, tampons, suppositories, body wipes, wound dressings such as bend aids and pads, skin patches, and suture material to form copper ion treatments that facilitate delivery or application of the copper ion-containing solution, and therefore the copper ions, to anatomical tissue. Creams, lotions, gels, foams and pastes may be used when it is advantageous to alter the consistency of the copper ion-containing solution from its original form to obtain a thicker copper ion treatment to facilitate its delivery or application to anatomical tissue. As a result of the copper ions contacting anatomical tissue when the copper ion treatments are applied thereto, local and systemic therapeutic effects are realized including antibacterial, antimicrobial, antiseptic, antifungal, antiviral, anti-pathogenic, anti-inflammatory, spermicidal, neutralization of free radicals, promotion of healing and tissue repair, prevention of biofilm, and immune-boosting effects. In particular, these effects are realized when the copper ion treatments are used on anatomical tissue in the genital-rectal areas, the oral-respiratory-otic areas and the dermatological areas of the body since the anatomical tissue in these areas is favorable for local and systemic delivery of drugs and medicaments.

In accordance with an aspect of the present invention, the copper ion-containing solution is combined with an appropriate topical cream base to form a copper ion-containing cream, i.e. copper ion cream, in which the amount of copper ion-containing solution is preferably in the range of 5% to 30% by weight of the total weight of the copper ion cream. Examples 5, 7 and 8 pertain to copper ion creams made in accordance with this aspect of the invention using the copper ion-containing solution of Example 1.

Example 5

An appropriate amount of copper ion-containing solution is combined with a biocompatible topical cream base to form a copper ion cream in which the copper ion-containing solution constitutes 5 percent of the total weight of the copper ion cream.

Example 6

An appropriate amount of copper ion-containing solution is combined with a biocompatible topical cream base to form a copper ion cream in which the copper ion-containing solution constitutes 10 percent of the total weight of the copper ion cream.

Example 7

An appropriate amount of copper ion-containing solution is combined with a biocompatible topical cream base to form a copper ion cream in which the copper ion-containing solution constitutes 20 percent of the total weight of the copper ion cream.

Example 8

An appropriate amount of copper ion-containing solution is combined with a biocompatible topical cream base to form a copper ion cream in which the copper ion-containing solution constitutes 30 percent of the total weight of the copper ion cream, brings about local and systemic therapeutic effects. Various topical cream bases can be used as the carrier for the copper ion-containing solution in order to form the copper ion creams of Examples 5, 6, 7 and 8. One suitable topical cream base that can be used is VersaBase® cream made by Professional Compounding Centers of America (PCCA) of Houston, Tex. Another suitable topical cream base that can be used in the copper ion creams is Vanicream® made by Pharmaceutical Specialties, Inc. of Rochester, Minn. The copper ion creams are effective against the body conditions being treated when the only active ingredient in the copper ion creams directed at the underlying condition is the copper ion-containing solution. However, the copper ion creams could contain other ingredients added to the topical cream base that are not active ingredients with respect to the underlying condition being treated such as preservatives, penetrating additives, bioadhesives and stability aids. Preferably, a total weight of at least 70 grams, more preferably 80 grams, of the copper ion creams in the various strengths, i.e. 5 percent, 10 percent 20 percent and 30 percent of copper ion-containing solution relative to the total weight of the copper ion cream, will be provided for use in containers, bottles, or tubes from which the copper ion creams can be dispensed. It should be appreciated that copper ion creams can be made using the alternative copper ion-containing solutions described above.

According to a further aspect of the present invention, a topical copper ion treatment in the form of a copper ion-containing gel, i.e. copper ion gel, is composed of the copper ion-containing solution and a suitable topical gel base as illustrated below by Examples 9, 10, 11 and 12, which utilize the copper ion-containing solution of Example 1. The amount of the copper ion-containing solution in the copper ion gel is preferably in the range of 5% to 30% by weight of the total weight of the copper ion gel.

Example 9

An appropriate amount of copper ion-containing solution is combined with a biocompatible topical gel base to form a copper ion gel in which the copper ion-containing solution constitutes 5 percent of the total weight of the copper ion gel.

Example 10

An appropriate amount of copper ion-containing solution is combined with a biocompatible topical gel base to form a copper ion gel in which the copper ion-containing solution constitutes 10 percent of the total weight of the copper ion gel.

Example 11

An appropriate amount of copper ion-containing solution is combined with a biocompatible topical gel base to form a copper ion gel in which the copper ion-containing solution constitutes 20 percent of the total weight of the copper ion gel.

Example 12

An appropriate amount of copper ion-containing solution is combined with a biocompatible topical gel base to form a copper ion gel in which the copper ion-containing solution constitutes 30 percent of the total weight of the copper ion gel.

Various topical gel bases can be used as a carrier for the copper ion-containing solution in order to form the copper ion gels. An example of a suitable topical gel base that can be used in Examples 9-12 is VersaBase® gel made by PCCA. As explained above for the copper ion creams, the copper ion gels will be effective when the only active ingredient in the copper ion gels is the copper ion-containing solution, but other ingredients that are inactive with respect to the underlying condition being treated can be added to the topical cream gels. Preferably, a total weight of at least 70 grams, more preferably 80 grams, of the copper ion gels in the various strengths, i.e. 5 percent, 10 percent, 20 percent and 30 percent of copper ion-containing solution relative to the total weight of the copper ion gel, is provided for use in containers, battles or tubes from which the copper ion gels can be dispensed. Also, copper ion gels can be made using the alternative copper ion-containing solutions. Copper ion gels can be made having a thin, fluidic consistency, and such gels may be used as copper ion serums.

A topical copper ion treatment in the form of a copper ion-containing lotion, i.e. copper ion lotion, according to an additional aspect of the invention is composed of the copper ion-containing solution and a suitable topical lotion base as represented by Examples 13, 14, 15 and 16. Examples 13-16 employ the copper ion-containing solution of Example 1, but copper ion lotions could be made using the alternative copper ion-containing solutions. The amount of the copper ion-containing solution in the copper ion lotion is preferably in the range of 5% to 30% by weight of the total weight of the copper ion lotion. Copper ion gels can be made having a thin, fluidic consistency, and such gels may be used as copper ion serums.

Example 13

An appropriate amount of copper ion-containing solution is combined with a biocompatible topical lotion base to form a copper ion lotion in which the copper ion-containing solution constitutes 5 percent of the total weight of the copper ion lotion.

Example 14

An appropriate amount of copper ion containing solution is combined with a biocompatible topical lotion base to form a copper ion lotion in which the copper ion-containing solution constitutes 10 percent of the total weight of the copper ion lotion.

Example 15

An appropriate amount of copper ion-containing solution is combined with a biocompatible topical lotion base to form a copper ion lotion in which the copper ion-containing solution constitutes 20 percent of the total weight of the copper ion lotion.

Example 16

An appropriate amount of copper ion-containing solution is combined with a biocompatible topical lotion base to form a copper ion lotion in which the copper ion-containing solution constitutes 30 percent of the total weight of the copper ion lotion.

Various topical lotion bases can be used as a carrier for the copper ion-containing solution in the copper ion lotions of Examples 13-16. One suitable topical lotion base that can be used is VersaBase® lotion made by PCCA. As explained above for the copper ion creams and gels, the copper ion lotions will be effective against the body conditions being treated when the only active ingredient in the copper ion lotions is the copper ion-containing solution, but other inactive ingredients could be added to the topical lotion base. Preferably, a total weight of at least 70 grams, more preferably 80 grams, of the copper ion lotions in the various strengths, i.e. 5 percent, 10 percent, 20 percent and 30 percent of copper ion-containing solution relative to the total weight of the copper ion lotion, will be provided for use in containers, bottles or tubes from which the copper ion lotions can be dispensed.

According to another aspect of the present invention, a topical copper ion treatment in the form of a copper ion-containing foam, i.e. copper ion foam, is composed of the copper ion-containing solution and a suitable foam base. Examples 17, 18, 19 and 20 set forth below pertain to copper ion foams or foamable solutions made in accordance with this aspect of the invention using the copper ion containing solution of Example 1, however copper ion foams or foamable solutions can be made using the alternative copper ion-containing solutions. The amount of the copper ion-containing solution in the copper ion foam or foamable solution is preferably in the range of 5% to 30% by weight of the total weight of the copper ion foam or foamable solution.

Example 17

An appropriate amount of copper ion-containing solution is combined with a biocompatible topical foam base to form a copper ion foam or foamable solution in which the copper ion-containing solution constitutes 5 percent of the total weight of the copper ion foam or foamable solution.

An appropriate amount of copper ion-containing solution is combined with a biocompatible topical foam base to form a copper ion foam or foamable solution in which the copper ion-containing solution constitutes 10 percent of the total weight of the copper ion foam or foamable solution.

Example 19

An appropriate amount of copper ion-containing solution is combined with a biocompatible topical foam base to form a copper ion foam or foamable solution in which the copper ion-containing solution constitutes 20 percent of the total weight of the copper ion foam or foamable solution.

An appropriate amount of copper ion-containing solution is combined with a biocompatible topical foam base to form a copper ion foam or foamable solution in which the copper ion-containing solution constitutes 30 percent of the total weight of the copper ion foam or foamable solution.

Various topical foam bases can be used as a carrier for the copper ion-containing solution in order to form the copper ion foams or foamable solutions. Depending on the foam base used in Examples 17-20, the combination of foam base and copper ion-containing solution may be in the form of a foam. Alternatively, some foam bases that may be used will result in a foamable solution when combined with the copper ion-containing solution, and the foamable solutions will typically require an appropriate dispenser to create the actual foam. An example of a suitable topical foam base that can be used is VersaBase® foam made by PCCA. When using VersaBase® as the foam base in Examples 17-20, a foamable solution is obtained and requires a foam dispenser to create the foam. As explained above for the copper ion creams, gels and lotions, the copper ion foams will be effective against the body conditions being treated with the only active ingredient therein being the copper ion-containing solution. However, other ingredients that are inactive with respect to the condition being treated can be added to the topical foam base. It is preferred that a total weight of at least 70 grams, more preferably 80 grams, of the copper ion foams or foamable solutions in the various strengths, i.e. 5 percent, 10 percent, 20 percent and 30 percent of copper ion-containing solution relative to the total weight of the copper ion foam or foamable solution, be provided in dispensers from which the copper ion foams can be dispensed.

According to a further aspect of the invention, a topical copper ion treatment in the form of a copper ion-containing paste, i.e. copper ion paste, is composed of the copper ion-containing solution and a suitable paste base. Example 21 set forth below pertains to a copper ion toothpaste made in accordance with this aspect of the invention using the copper ion-containing solution of Example 1, but copper ion pastes can also be made using the alternative copper ion-containing solutions. The amount of the copper ion-containing solution in the copper ion pastes is preferably in the range of 5% to 30% by weight of the total weight of the copper ion paste.

Example 21

An appropriate amount of copper ion-containing solution is combined with a toothpaste base material to form a copper ion toothpaste in which the copper ion-containing solution constitutes in the range of 5 percent to 30 percent of the total weight of the copper ion toothpaste.

The toothpaste base material used in Example 21 can be a commercially available toothpaste including any of the toothpastes marketed and sold under the major brand names. A toothpaste made in accordance with Example 21 is advantageous for treating bad breath, sore gums, gum disease and tooth decay when used on a daily basis in place of a person's regular toothpaste.

According to a further aspect of the invention, the copper ion-containing solution can be combined with various base solutions to form alternative copper ion solutions. Example 22 set forth below pertains to a copper ion mouthwash made in accordance with this aspect of the invention using the copper ion-containing solution of Example 1, but copper ion solutions can also be made using the alternative copper ion-containing solutions of Examples 2-4. The amount of copper ion-containing solution in the alternative copper ion solution is preferably in the range of 5% to 30% by weight of the total weight of the alternative copper ion solution.

Example 22

An appropriate amount of copper ion-containing solution is combined with a mouthwash base solution to form a copper ion mouthwash in which the copper ion-containing solution constitutes in the range of 5 percent to 30 percent of the total weight of the copper ion mouthwash.

The mouthwash base solution used in Example 22 can be a commercially available mouthwash including any of the mouthwashes marketed and sold under the major brand names. A mouthwash made in accordance with Example 22 is advantageous for treating bad breath, sore gums, periodontal disease and tooth decay when used on a daily basis.

The examples described above pertaining to carriers in the nature of lotions, gels, foams and other solutions are particularly well suited for creating copper ion treatments in the nature of copper ion soaps by using as carriers lotion, gel, foam or other solution bases containing a soap component. The copper ion soaps could be designed for use as body soaps or as dish soaps.

Figure 1:
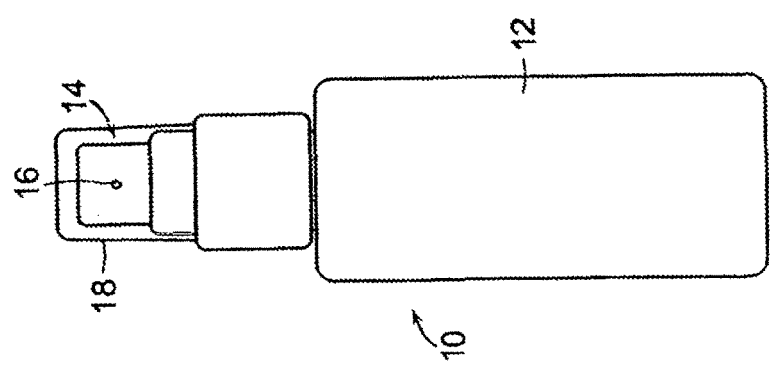
FIG. 1 is a front view of a bottle containing a copper ion treatment and having a spray pump nozzle for dispensing the copper ion treatment.

FIG. 1 depicts a device 10 useful for dispensing the copper ion treatments, particularly the copper ion-containing solutions in their original form, e.g. the form resulting from Examples 1-4, and the copper ion lotions. The device 10 comprises a container or botte 12 for holding the copper ion-containing solution and having a spray pump nozzle 14 with an outlet orifice 16. The spray pump nozzle 14 is resiliently biased, typically by a spring, in an upward direction away from the container 12 but is depressible in a downward direction toward the container 12 to effect the spray pump action. Each time the spray pump nozzle is manually depressed the full amount, typically using a finger of the hand holding the container, a predictable amount of copper ion-containing solution is discharged in the form of a spray or stream from the outlet orifice 18. The container 12 may include a removable protective cover 18 for being disposed over the spray pump nozzle 14 between uses. In use, the outlet orifice 16 is placed in line with anatomical tissue to be treated at a close enough distance that the tissue is within the range of the spray or stream dispensed from the outlet orifice. The spray pump nozzle 14 is then depressed the full amount using a finger, causing the predictable amount of copper ion-containing solution to be delivered or sprayed onto the anatomical tissue. The spray pump nozzle 14 can, of course, be depressed multiple times to deliver multiple sprays or streams of the copper ion-containing solution to the tissue. The device 10 is particularly useful for dispensing the copper ion-containing solution in its original form to contact anatomical tissue within the mouth and throat, anatomical tissue of the skin, and anatomical tissue of the external genital and rectal areas. The device 10 could also be adapted to dispense the copper ion lotions, although in such case the copper ion lotions would typically be dispensed in the form of a ribbon, mass or stream of material. In the latter case, the copper ion lotions could be dispensed directly on the tissue to be treated, or on the palm or fingers of a hand which is then used to apply the lotions on the tissue to be treated. The copper on lotions may be best suited for use on the skin, on the external genital and rectal areas, and in the vagina.

Figure 2:
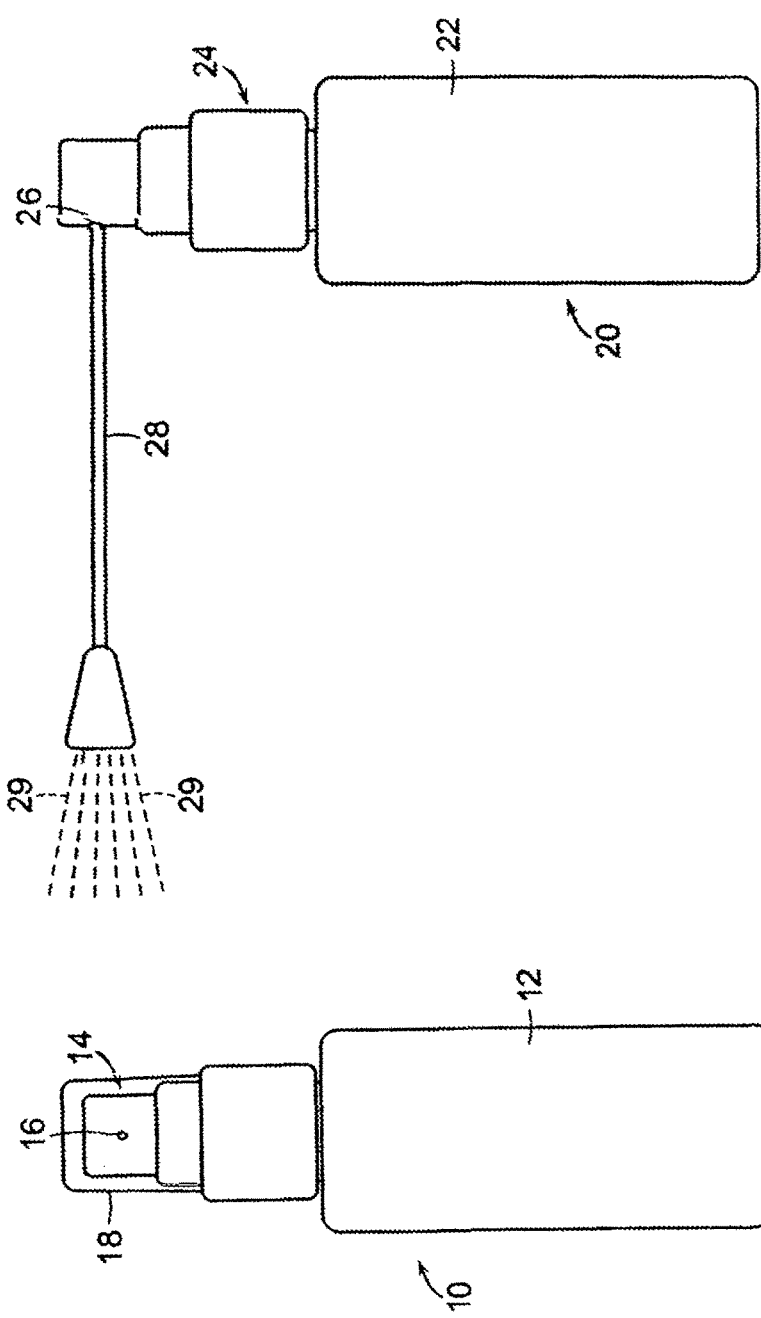
FIG. 2 is a side view of a bottle containing a copper ion treatment and having a spray pump nozzle with an elongate extension for dispensing the copper ion treatment.

Another device 20 useful for dispensing the copper ion treatments, particularly the copper ion-containing solution in its original form, is shown in FIG. 2. The device 20 is similar to the device 10 and comprises a container or bottle 22 having a spray pump nozzle 24 with an outlet orifice 26. The device 20, however, further includes an elongate hollow extension 28 attached to the spray pump nozzle 24. The extension 28 has a first end coupled with the outlet orifice 26 of the spray pump nozzle 24 and has an opposed second end with a wider end surface having a discharge opening 29. Preferably, a plurality of discharge openings 29 are provided along the wider end surface as shown in dotted lines in FIG. 2 to obtain a wider spray pattern as indicated by dotted lines. Each time the spray pump nozzle 24 is manually depressed the full amount, a predictable amount of copper ion treatment is released in spray form from the discharge openings 29 at the end of the extension 28. The wider end surface and plurality of discharge openings at the second end of the extension provides a wider spray pattern than the device 10. The device 20 could be designed without the spray pump nozzle, with the container 22 being squeezable to force the copper ion treatment to be discharged from the discharge opening(s) 29. The extension 28 may be selectively detachable/attachable to the spray pump nozzle 24 for ease of storage of the device 20. The device 20 may include a removable protective cover (not shown) for being placed over the nozzle 24 between uses. The device 20 is particularly useful as an atomizer for dispensing the copper ion treatments to contact anatomical tissue deeper within the mouth, throat and airway.

The device 30 depicted in FIG. 3 is also useful for dispensing the copper ion treatments, particularly the copper ion-containing solution in its original form. The device 30 comprises a squeezable container or bottle 32 for holding the copper ion treatment and having a tapered dropper or extension 34 with an outlet orifice 36 attached to a cap on the container 32, in use, the container 32 is positioned so that the outlet orifice 36, which is located at the tip of the dropper, faces anatomical tissue to be treated. The container 32 is then squeezed with the fingers and, in response to such finger pressure. Individual drops of a predictable amount of copper ion treatment are released from the outlet orifice 36. Alternatively, the extension 34 can be designed to discharge the copper ion treatment in the form of a spray as shown in dotted lines in FIG. 3, which would be particularly useful as a nasal/ear spray. The tapered configuration of the dropper/extension 34 facilitates its placement in the nostril (nasal cavity) and ear (ear canal). The container 32 may include a removable protective cover 38 for being disposed over the dropper 34 between uses. The device 30 is particularly useful for dispensing the copper ion treatments to contact anatomical tissue within the nose (nostrils) and ears (ear canal), and on the skin and nails.

Figure 4:
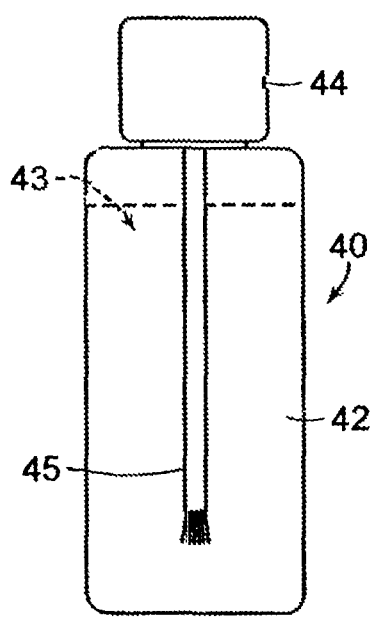
FIG. 4 is a side view of a bottle containing a copper ion treatment and having a brush for applying the copper ion treatment to anatomical tissue.

An additional device 40 for dispensing the copper ion treatments is shown in FIG. 4. The device 40 comprises a container or bottler 42 for holding the copper ion treatment and having a removable cap 44 with a brush 45 attached to an underside of the cap. Typically, the cap 44 will be screwed onto a neck of the container 42. When the cap 44 is disposed on the container 42, the brush 45 extends into the container and is disposed within the copper ion treatment 43. Upon removal of the cap 44 from the container 42, the cap 44 may be manipulated using the fingers and hand to contact anatomical tissue to be treated with the brush 45 in order to deposit the copper ion treatment from the brush 45 onto the anatomical tissue. The device 40 would be particularly useful for applying the copper ion treatments on the skin and nails. The brush 45 could be eliminated from the cap 44, in which case the device 40, if sized appropriately, would be advantageous for holding a copper ion solution such as a copper ion mouthwash.

Figure 5:
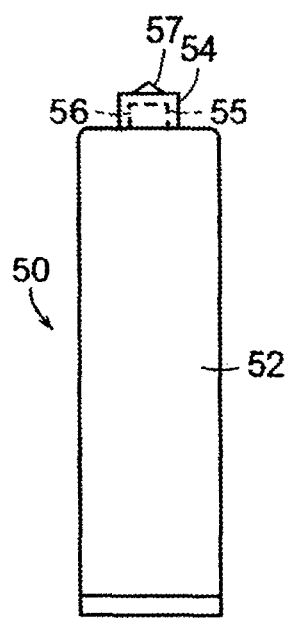
FIG. 5 is a side view of a tube containing a copper ion treatment wherein the tube is squeezable to dispense the copper ion treatment.

The device 60 illustrated in FIG. 5 is particularly useful for dispensing the copper ion treatments formed as creams, lotions, gels and pastes. The device 50 comprises a container 52 in the form of a squeezable tube for holding the copper ion treatment and having a removable cap 54 disposed on an open end or neck 56 of the tube. Typically the cap 54 will be threaded onto an external thread 55 on the neck 56 of the tube. The cap 54 may optionally have a piercing formation 57 that may be used to puncture an optional seal covering the open neck 56 prior to the first use. Upon removal of the cap 54, the piercing formation 57 is placed against the seal, and the cap 54 is pushed in the direction of the tube 52 to puncture the seal. Once the seal is penetrated, the tube 52 can be squeezed, preferably from the bottom of the tube working upward, causing the copper ion treatment to be dispensed from the open neck 56 of the tube. The device 50 is particularly well suited for dispensing the copper ion treatments onto the fingers or palm of a hand that is then used to apply the treatments to anatomical tissue, particularly the tissue of the skin and the external genital and rectal areas. However, the copper ion treatments could be squeezed directly on the anatomical tissue to be treated. In addition, when the copper ion treatment is in a paste or other suitable form for use as a toothpaste, the device 50 is particularly well suited for dispensing the copper ion treatment onto a tooth brush in a conventional manner. As explained further below, the device 50 is particularly well suited for use with a vaginal applicator.

Figure 6:
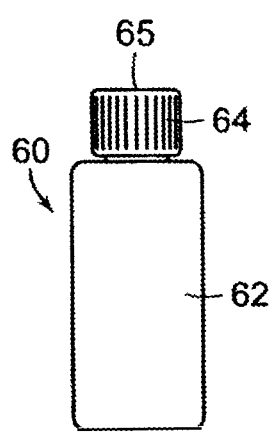
FIG. 6 is a side view of an alternative bottle that is squeezable to dispense a copper ion treatment and showing the bottle in a closed condition.
Figure 7:
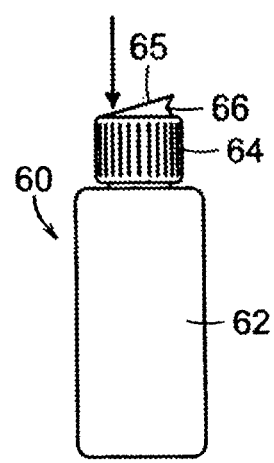
FIG. 7 is a side view of the botte of FIG. 6 showing the bottle in an open condition.

FIGS. 6 and 7 depict an additional device 60 useful for dispensing the copper ion treatments. The device 60 is particularly advantageous for dispensing copper ion lotions. The device 60 comprises a container or bottle 62 for holding the copper ion treatment and having a cap 64 disposed on an open end or neck of the bottle. The cap 64 could be removable or non-removable. The top surface of the cap 64 is formed by a pivotable member or disc 65 having an outlet orifice 66 along a side edge thereof. FIG. 6 depicts the cap 64 in its closed condition wherein the pivotable member 65 is in a horizontal position relative to the cap 64 and the outlet orifice 66 is disposed within the cap 64 and is not exposed. When the pivotable member 65 is depressed downwardly toward the container 62 at a location opposite the outlet orifice 66 as shown by the arrow in FIG. 7, the cap 64 will assume the open condition shown in FIG. 7 wherein the pivotable member 65 is disposed at an angle relative to the cap 64 and the outlet orifice 66 is in an exposed position located slightly above the cap 64, in use, the pivotable member 65 would be depressed using pressure applied with one or more fingers of the hand. With the cap 64 in the open condition as shown in FIG. 7, the container 62 can be squeezed manually to dispense the copper ion treatment therein from the outlet orifice 66. The cap 64 is returned to the closed position by pressing downwardly on the pivotable member 65 at a location adjacent the outlet orifice. The device 60 is advantageous for dispensing the copper ion treatments onto the palm of the hand or fingers used to apply the treatment to anatomical tissue to be treated, but the device 60 could be used to dispense the copper ion treatments directly on the anatomical tissue to be treated.

Figure 8:
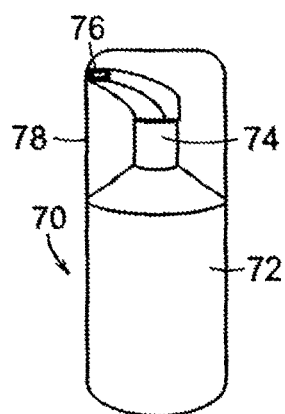
FIG. 8 is a side view of a bottle containing a copper ion treatment and having a pump nozzle for dispensing the copper ion treatment in the form of foam.

The device 70 shown in FIG. 8 is an example of a device that can be used to dispense the copper ion treatment in the form of a copper ion foam. The device 70 comprises a container 72 for holding the copper ion foam or foamable solution and having a resiliently biased foam pump dispenser 74 with an outlet orifice 76. When the foam pump dispenser 74 is depressed the full amount in a manner similar to the device 10, a predictable amount of the copper ion foam is discharged through the outlet orifice 76. If necessary, the device 70 may include a mechanism for creating foam as the copper ion treatment is discharged therefrom. The device 70 may have a removable protective cover 78 for being disposed over the foam pump dispenser 74 between uses. The device 70 could also be adapted to dispense copper ion lotions and gels.

Figure 9:
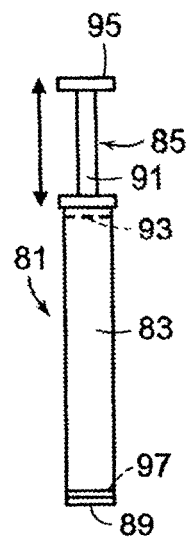
FIG. 9 is a side view of an applicator for delivering a copper ion treatment to the vagina.
Figure 10:
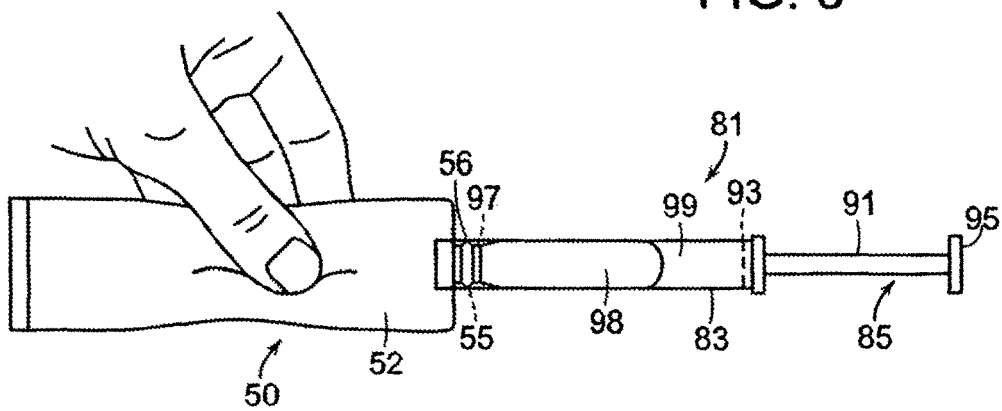
FIG. 10 is a side view of the applicator of FIG. 9 showing use of the applicator in conjunction with the tube of FIG. 5.

FIG. 9 depicts a vaginal applicator 81 useful for delivering the copper ion treatments to the vagina. The vaginal applicator 81 is particularly useful in conjunction with the device 50 as depicted in FIG. 10. Also, the vaginal applicator 81 is particularly well suited for use when the copper ion treatments are in the form of either lotion, cream or gel. The vaginal applicator 81 comprises a hollow barrel 83 and a plunger 85 slidably mounted in the hollow barrel 83. The barrel 83 has an open forward end defining a discharge opening 89 and has a rearward end wall through which a stem 91 of the plunger passes. The stem 91 is attached at one end thereof to an internal flange 93 disposed within the barrel in close, sealing relation therewith. The plunger has a finger flange 95 attached to an opposite end of the stem 91 that is disposed external of the barrel 83, the flange 95 being engageable with a finger or fingers of a hand in order to selectively depress and withdraw the plunger 85 relative to the barrel 83. For use with the device 50, the forward end of the barrel 83 is provided with an internal thread 97 to threadedly engage with the external thread 55 on the neck 56 of the tube 52.

FIG. 10 lustrates the vaginal applicator 81 being filled with the copper ion treatment from the tube 52 of the device 50. As seen in FIG. 10, the cap 54 is removed from the neck 56 of the tube 52, and the forward end of the barrel 83 is threaded onto the neck 56 via threaded engagement of the threads 55 and 97. At this stage, the plunger 85 is fully withdrawn relative to the barrel 83 such that the internal flange 93 is in abutment with the rearward end wall of the barrel 83. The tube 52 is then squeezed using pressure from the fingers in order to dispense the copper ion treatment, represented at 98, into the barrel 83 from the open neck 58 of the tube 52. When the barrel 83 is sized for a particular dosage of copper ion treatment, a sufficient amount of copper ion treatment can be dispensed from the tube 52 to entirely fill the space within the barrel 83 from the neck of the tube 56 to the internal flange 93 which is in abutment with the rearward end wall of the barrel. Alternatively, an indicia or other marking 99 can be provided on the barrel 83 to indicate the point to which the barrel 83 should be filed with copper ion treatment 98 from the tube 52. It is preferred that filling the space within the barrel from the neck of the tube to the internal flange corresponds to a dose of 5 grams of the copper ion treatment. Once the barrel 83 has been filled with the appropriate amount of copper ion treatment 98, the barrel 83 is disengaged from the neck 56 of the tube 52 by disengaging the thread 97 from the thread 55. In order to dispense the copper ion treatment 98 from the applicator 81, the finger flange 95 of the plunger 85 is depressed toward the barrel 83 using a finger, thereby causing the internal flange 93 to push the copper ion treatment 98 through the discharge opening 89 as the plunger 85 is depressed relative to the barrel 83. When the finger flange 95 meets the rearward end wall of the barrel 83, the copper ion treatment 98 will be fully discharged from the applicator. It should be appreciated that the applicator 81 could be used in conjunction with other devices for supplying the copper ion treatments to the barrel 85. It should also be appreciated that the applicator 81 can be supplied for use pre-filled with copper ion treatment 98, in which case the forward end of the barrel would be provided with a removable cap or seal. The applicator 81 is particularly advantageous for supplying the copper ion treatments to the vagina. Accordingly, prior to depressing the plunger 85 to discharge the copper ion treatment 98 from the barrel 83, the forward end of the barrel 83 would be introduced into the vagina until the rearward end of the barrel was located near the entrance to the vagina. Then, upon depressing the plunger 85, the copper ion treatment 98 is discharged from the discharge opening 89 into the vagina.

Figure 11:
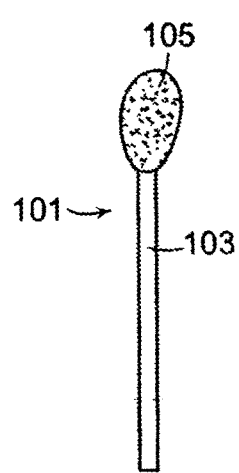
FIG. 11 is a side view of an alternative applicator for applying a copper ion treatment onto anatomical tissue.

Another type of applicator useful in applying the copper ion treatments to anatomical tissue is shown at 101 in FIG. 11. The applicator 101 is in the nature of a swab comprising a handle 103 and a body of absorbent material 105 at an end of the handle 103. The applicator 101 can be used in conjunction with a container or bottle containing a copper ion treatment, such as the device 40 of FIG. 4. Upon removal of the cap 44 from the bottle 42 of the device 40, the handle 103 of the applicator 101 can be grasped with a hand used to manipulate the applicator 101 in order to dip the body of absorbent material 105 into the copper ion treatment within the bottle 42. The body of absorbent material 105 can then be gently contacted with anatomical tissue to be treated thereby causing the copper ion treatment carried by the absorbent body 105 to be deposited on the anatomical tissue to be treated. The applicator 101 is best suited for applying copper ion treatments to localized areas of the skin, nails, ear canal, nostrils, mouth and throat. Of course, it should be appreciated that swab applicators 101 can be provided in sealed packages with the bodies of absorbent material 105 pre-supplied with copper ion treatment.

Another type of carrier that can be used to deliver copper ion treatments to the vagina is a tampon. The tampon used can be a commercially available tampon or one similar thereto. The tampon can be one having an applicator including a barrel containing the absorbent tampon body and a plunger slidable within the barrel to dispose or eject the absorbent tampon body from an open forward end of the barrel once the forward end has been introduced in the vagina an appropriate distance in a commonly known manner of tampon use. In this case, an appropriate amount of copper ion treatment can be supplied to the absorbent tampon body via the open forward end of the barrel prior to introduction of the applicator in the vagina and ejection of the absorbent tampon body from the applicator into the vagina. Another suitable tampon can be one without an applicator, i.e. a digital tampon, where the absorbent tampon body is inserted in the vagina by pushing it with the fingers. In this case, the appropriate amount of copper ion treatment is simply deposited on the absorbent tampon body prior to its insertion in the vagina. In both cases, unless the tampon is going to be inserted in the vagina immediately or soon after the absorbent tampon body has been provided with the appropriate amount of copper ion treatment, the tampon should be stored in a sealed container or package until the time of its use in order to avoid evaporation of the copper ion treatment, it should be appreciated that tampon bodies to which the copper ion treatment has been supplied can be provided in sealed containers or packages, with or without an applicator, as a ready-to-use commercial product. Alternatively, the appropriate amount of copper ion treatment may be deposited by the user on the absorbent tampon bodies of tampons sold separately or in conjunction with the copper ion treatment. Preferably, the tampon bodies are supplied with an amount of copper ion-containing solution in the range of 5 to 10 milliliters.

Figure 12:
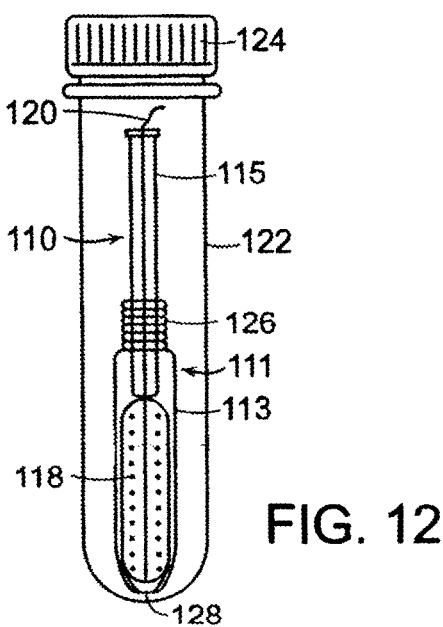
FIG. 12 is a side view of a tampon having a tampon body used as a carrier to deliver a copper ion treatment to the vagina.

FIG. 12 lustrates a tampon 110 according to an aspect of the present invention including an applicator 111 having a hollow barrel 113 and a hollow plunger 115, and an absorbent tampon body 118, to which the appropriate amount of copper ion treatment has been supplied, disposed in the barrel 113 with the string 120 of the tampon body extending from a rear end of the plunger 115. The plunger 115 is slidable within and toward the barrel 113 to push the tampon body 118 and eject it from an open forward end 128 of the barrel. The forward end 128 of the barrel 113 can be tapered to facilitate introduction and advancement in the vagina and can be provided with sifts that expand as the tampon body 118 passes therethrough. The tampon 110 is provided in an air-tight container or bottle 122 having a removable cap or lid 124. In order to use the tampon 110, the lid 124 is removed from the bottle 122 and the tampon 110 is removed from the bottle. The tampon 110 is inserted in the vagina in a conventional manner of using tampons. More specifically, the applicator 111 is held by grasping a finger grip 126 on the barrel 113, and the forward end 128 of the barrel is inserted in the vagina. The applicator 111 is advanced into the vagina until the fingers grasping the finger grip 126 touch the entrance to the vagina. The plunger 115 is then pushed into the barrel 113, thus causing the tampon body 118 to be ejected from the forward end 128 of the barrel into the vagina. The applicator 111 is then withdrawn from the vagina and discarded, leaving the tampon body 118 in place in the vagina. Once the tampon body 118 is in place in the vagina, the copper ion treatment carried by the tampon body contacts the anatomical tissue of the vagina and leaks into the vaginal fluid normally present in the vagina. The tampon body 118 is removed from the vagina at the appropriate time by grasping and pulling on the string 120. Examples of tampons according to an aspect of the invention are described below in Examples 23 and 24.

Example 23

A tampon for delivering a copper ion treatment to the vagina is prepared by supplying 5 milliliters of a copper ion-containing solution to an absorbent tampon body intended to be introduced into the vagina.

Example 24

A tampon for delivering a copper ion treatment to the vagina is prepared by supplying 10 milliliters of a copper ion-containing solution to an absorbent tampon body intended to be introduced into the vagina.

The copper ion-containing solution used in Examples 23 and 24 is the copper ion-containing solution in its original form as obtained in accordance with the method set forth in Example 1. However, it should be appreciated that tampons can be provided in which the tampon bodies are supplied with the alternative copper ion-containing solutions or other forms of the copper ion treatments.

Another type of carrier useful to deliver the copper ion treatments to the vagina and rectum is a suppository. Suppositories are commonly used in the vagina and rectum (anus) as a means for dispensing various active ingredients or medicaments. Suppositories are made in various shapes including oviform, globular, conical and bullet shapes, and in various sizes. Suppositories typically weigh in the range of 1 to 5 grams. Suppositories can be solid bodies composed of a mixture of a suitable suppository base material and the active ingredients or medicaments. Alternatively, suppositories can be made with a solid outer wall of suppository base material enclosing non-solid active ingredients or medicaments. The suppository base materials used in suppositories allow them to dissolve or melt when exposed to the moisture (body fluid) or heat (body temperature) found in the vagina or rectum (rectal or anal canal), thereby releasing the active ingredients or medicaments into the vagina or rectum. Suitable suppository base materials include oleaginous (fatty) base materials, including cocoa butter, theobroma oil and synthetic triglycerides, or water soluble or miscible base materials, including glycerinated gelatin and polyethylene glycol (PEG) polymers. It is preferred that the base materials be non-toxic, non-irritating, inert, and biocompatible. Suppositories suitable for use in an aspect of the present invention can be prepared in various ways according to conventional methods for preparing suppositories including compression molding and fusion molding. Suppositories for use as vaginal and rectal suppositories according to an aspect of the present invention are preferably made in two different sizes, i.e. a suppository weighing 3 grams and a suppository weighing 5 grams, to accommodate different sizes of vaginal and rectal anatomy. Each size suppository can be made indifferent strengths based on the percentage by weight of the active ingredient, i.e. the copper ion treatment, relative to the total weight of the suppository. Preferably, the amount of copper ion-containing solution in the suppository is in the range of 5% to 30% of the total weight of the suppository. The suppositories are preferably formed in plastic molds and can be stored at room temperature. The suppositories will be effective against the body condition being treated when the only active ingredient contained in the vaginal and rectal suppositories is the copper ion treatment. However, the vaginal and rectal suppositories could contain additional ingredients that are inactive with respect to the underlying condition or conditions being treated, such as preservatives, penetrating additives, bioadhesives and stability aids. The suppositories may be inserted in the vagina and rectum using the fingers, or the suppositories may be provided with applicators to facilitate insertion thereof in the vagina and rectum. Examples of vaginal and rectal suppositories according to an aspect of the invention are set forth in Examples 25-32, which utilize the copper ion-containing solution of Example 1. However, the alternative copper ion-containing solutions could be used in Examples 25-32.

Example 25

A suppository base material is combined with an appropriate amount of copper ion-containing solution and is molded into a suppository for vaginal or rectal use having a total weight of 3 grams, wherein the copper ion-containing solution constitutes 5 percent of the total weight of the suppository.

Example 26

A suppository base material is combined with an appropriate amount of copper ion-containing solution and is molded into a suppository for vaginal or rectal use having a total weight of 3 grams, wherein the copper ion-containing solution constitutes 10 percent of the total weight of the suppository.

Example 27

A suppository base material is combined with an appropriate amount of copper ion-containing solution and is molded into a suppository for vaginal or rectal use having a total weight of 3 grams, wherein the copper ion-containing solution constitutes 20 percent of the total weight of the suppository.

Example 28

A suppository base material is combined with an appropriate amount of copper ion-containing solution and is molded into a suppository for vaginal or rectal use having a total weight of 3 grams, wherein the copper ion-containing solution constitutes 30 percent of the total weight of the suppository.

Example 29

A suppository base material is combined with an appropriate amount of copper ion-containing solution and is molded into a suppository for vaginal or rectal use having a total weight of 5 grams, wherein the copper ion-containing solution constitutes 5 percent of the total weight of the suppository.

Example 30

A suppository base material is combined with an appropriate amount of copper ion-containing solution and is molded into a suppository for vaginal or rectal use having a total weight of 5 grams, wherein the copper ion-containing solution constitutes 10 percent of the total weight of the suppository.

Example 31

A suppository base material is combined with an appropriate amount of copper ion-containing solution and is molded into a suppository for vaginal or rectal use having a total weight of 5 grams, wherein the copper ion containing solution constitutes 20 percent of the total weight of the suppository.

Example 32

A suppository base material is combined with an appropriate amount of copper ion-containing solution and is molded into a suppository for vaginal or rectal use having a total weight of 5 grams, wherein the copper ion-containing solution constitutes 30 percent of the total weight of the suppository.

Figure 13:
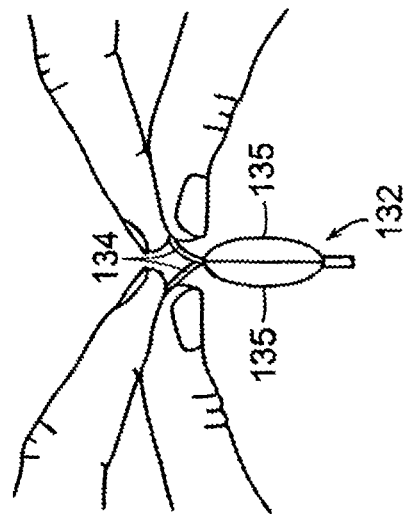
FIG. 13 is a broken front view of a plurality of suppositories containing a copper ion treatment, the suppositories being insertable in the vagina or rectum to deliver the copper ion treatment to the vagina or rectum.
Figure 14:
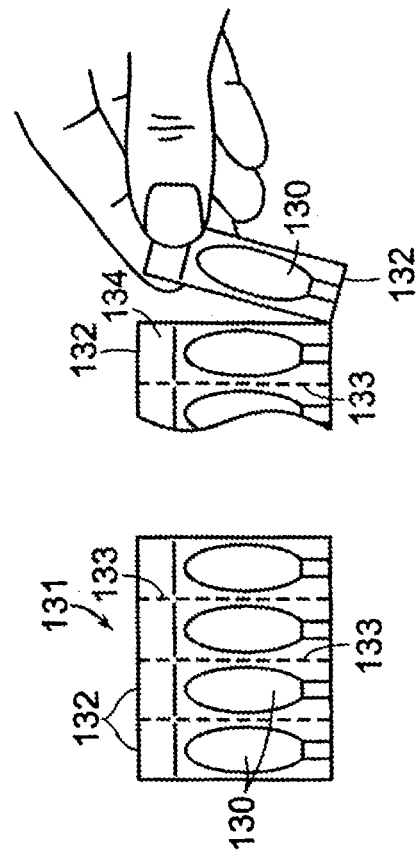
FIG. 14 is a side view showing a suppository of FIG. 13 being removed from its package.

FIG. 13 illustrates a strip 131 of interconnected packages or pods 132, each enclosing a vaginal or rectal suppository 130 containing a copper ion treatment. The pods 132 are separated from each other by a perforation line 133 allowing the pods 132 to be detached from each other by tearing along the perforation lines 133 as depicted in FIG. 13. Each pod 132 has front and rear walls 135 between which a suppository 130 is retained. The front and rear walls 135 are sealed to one another along their peripheral edges. As shown in FIG. 14, each pod 132 is provided with a pair of finger tabs 134 respectively attached to the front and rear walls 135, the finger tabs 134 being capable of being pulled in opposite directions using the fingers to separate the opposed walls 135 and thereby release the suppository 130 contained therein.

Figure 15:
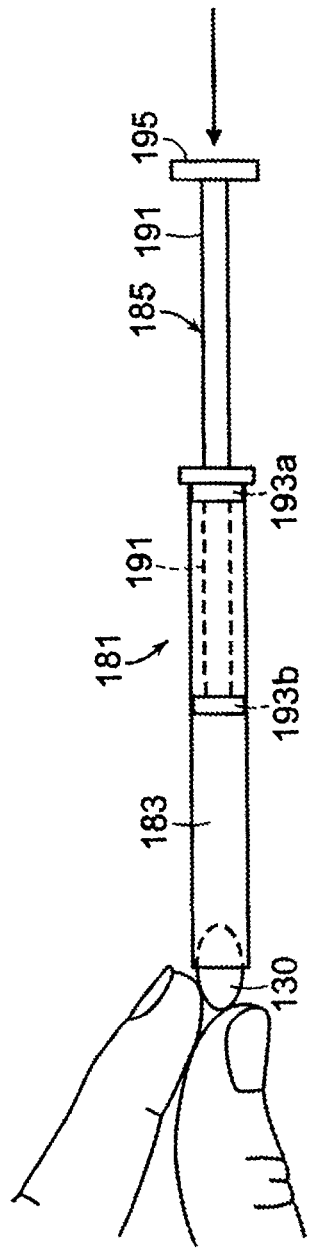
FIG. 15 is a side view of an applicator for delivering the suppositories of FIG. 13 to the vagina or rectum.

FIG. 16 illustrates an applicator 181 suitable for use in delivering a suppository 130 to the vagina or rectum. The applicator 181 is similar to the applicator 81 but does not have an internal thread at the forward end of the barrel 183. In addition, the plunger 185 of the applicator 181 has two internal flanges 193a and 193b within the barrel 183, the flange 193a controlling the distance that the plunger can be withdrawn relative to the barrel and the flange 193b serving to eject the suppository from the barrel when the plunger is depressed the full amount. In use, a suppository 130 is manually positioned in the open forward end of the barrel 183 as illustrated in FIG. 15. The open forward end of the barrel 183 is preferably sized to retain the suppository 130 in position without being overly snug or tight. The plunger 185 is withdrawn the full amount relative to the barrel 183, which coincides with abutment of internal flange 193a with the rearward end wall of the barrel 183. The forward end of the barrel 183 holding the suppository is then introduced in the vagina or rectal (anal) canal, and the applicator 181 is gently pushed into the vagina or rectal canal until the fingers holding the rearward end of the barrel 183 are adjacent or touch the entrance to the vagina or rectal canal. The finger flange 195 is then depressed to push the plunger 185 toward and into the barrel 183 as shown by the arrow in FIG. 15, thus causing the flange 193b to engage the suppository 130 and eject it from the forward end of the barrel into the vagina or rectal canal. The applicator 181 is then removed from the vagina or rectal canal, leaving the suppository in the vagina or rectal canal. The suppository will melt or dissolve in the vagina or rectal canal such that the copper ion treatment is released to contact anatomical tissue of the vagina or rectal canal and to mingle with body fluid present in the vagina or rectal canal.

Another type of carrier that can be used to deliver the copper ion treatments to anatomical tissue is a body wipe. FIG. 16 lustrates a body wipe 200 contained in a sealed package 202 having front and rear walls 203. The body wipe 200 comprises a thin sheet of material disposed in a folded condition when retained between the front and rear walls 203, which are sealed along their peripheral edges. The body wipe 200 enclosed between the front and rear walls 203 contains a wet or moist copper ion treatment. The front and rear walls 203 may be grasped by the fingers at corresponding corners thereof and pulled in opposite directions similar to the pods 132 in order to separate the front and rear walls 203 and thereby allow the body wipe 200 to be removed from the package 202. FIG. 16 shows the package 202 in a partially open condition in which corresponding corner sections of the front and rear walls 203 have been peeled away from one another thereby providing access to the body wipe 200. Upon removal from the package 202, the body wipe 200 can be unfolded to its full size, which is substantially larger than its size in the folded condition, and can be used to wipe anatomical tissue to be treated causing the copper ion treatment to be transferred to the anatomical tissue. The body wipe 200 is advantageous for applying the copper ion treatments to the skin and the external genital and rectal areas.

Another type of carrier for the copper ion treatments is a wound dressing, such as a band aid, gauze pad or similar device. Such carriers can be selected from products that are commercially available for removable application to the skin to temporarily cover and protect an affected area of the skin. FIG. 17 depicts a carrier in the nature of a wound dressing 300 having a surface 301 for being placed in contact with the skin. The surface 301 includes a protective surface 302 for being positioned over a wound, and an adhesive border 303 surrounding the surface 302. In use, a copper ion treatment, such as the copper ion-containing solution in original form, can be liberally sprayed onto the surface 302 of the carrier that is applied adjacent or in contact with the skin. Then, when the surface 302 of the carrier is applied adjacent or in contact with the skin and the carrier is left in place on the skin for a period of time, the copper ions contact or are transferred to the skin and provide the therapeutic effects described above. Of course, it would be possible to provide carriers of this type in sealed packages in which the carriers are pre-supplied or pre-treated with the copper ion treatment similar to the body wipe 200.

A further type of carrier for the copper ion treatments is a skin patch, such as a dermal patch or a transdermal patch, represented at 400 in FIG. 18. The skin patch 400 has a drug delivery surface 401 containing the copper ion treatment surrounded by adhesive border 402. The patch is applied to the skin and left in place for a period of time causing the copper ions to diffuse through the skin where they can act locally or penetrate the capillaries for broader systemic effects. Examples of suitable transdermal patches are the transdermal and microneedle 3M Drug Delivery Systems manufactured by 3M Corporation.

An additional type of carrier for the copper ion treatments is suture material represented at 500 FIG. 19, used by medical professionals to close or suture external or internal incisions or wounds, i.e. "stitches". Prior to using the suture material 500, which can be conventional suture material, the suture material can be soaked in the copper ion-containing solution for a period of time in order to cover or saturate the suture material with the solution. Suture material can also be store in sealed packages containing the copper ion-containing solution. Then, when the suture material is used to create sutures or stitches in anatomical tissue T as seen in FIG. 19, the copper ions in the solution contact the anatomical tissue and provide the therapeutic effects previously described.

The copper ion-containing solution and the other forms of copper ion treatments described herein can be used on anatomical tissue in various areas of the body including the genital-rectal areas (vagina, vulva, penis, scrotum, rectum (anus), rectal (anal) canal and surrounding anatomical areas), the oral-respiratory-otic areas (mouth, throat, airway, nostrils and ears) and the dermatological areas (skin and nails) of the body. The treatment effects provided by the copper ion treatments encompass treatment of active or existing disease and other undesirable body conditions as well as the prevention of such diseases and conditions. The copper ion treatments are especially beneficial for their ability to kill or neutralize harmful or undesired pathogens and microbes including bacteria, viruses and fungi. Although the copper ion treatments are applied topically to anatomical tissue and have a localized effect on diseases and undesirable body conditions affecting the anatomical tissue, the copper ion treatments also have a broader systemic effect on diseases and undesirable body conditions. The effects realized with the copper ion treatments include antibacterial, antimicrobial, antiseptic, antifungal, antiviral, anti-pathogenic, anti-inflammatory, spermicidal, neutralization of free radicals, promotion of healing and tissue repair, prevention of biofilm, and immune-boosting effects. The diseases or conditions affecting the genital-rectal areas that are treatable with the copper on treatments include vaginitis, bacterial vaginosis, hemorrhoids, vaginal dryness, imbalances in vaginal pH, bacterial infections caused by gonorrhea, chlamydia, *streptococcus* and *staphylococcus*, protozoan infections caused by trichomonas, pelvic inflammatory disease, viral infections caused by herpes (I and II), HPV and HIV, fungal infections caused by yeast, candida, thrush and other fungi, exposure to sexually transmitted diseases, and the risk of undesired pregnancy (contraception). The diseases or conditions affecting the oral-respiratory-otic areas that are treatable with the copper ion treatments include bacterial infections caused by gonorrhea, chlamydia, *streptococcus* and *staphylococcus*, protozoan infections caused by trichomonas, viral infections caused by herpes (I and II), HPV and HIV, canker sores, mouth sores, mouth ulcers, colds, sinusitis, rhinosinusitis, sore throat, nasal discharge, congestion, runny nose, bronchitis, allergies, asthma, tonsillitis, wheezing, sneezing, ear infections, earache, pressure in the ears, cough, hoarseness, laryngitis, sore gums, periodontal disease, bad breath and tooth decay. The diseases or conditions affecting the dermatological areas that are treatable with the copper ion treatments include bacterial infections caused by *staphylococcus, streptococcus, enterobacter, E. coli* and *pseudomonas*, viral infections caused by shingles, herpes (I and II) and HPV, fungal infections such as athlete's foot, ringworm and toenail fungus, impetigo, rosacea, psoriasis, eczema, warts, sun/wind damage, dry skin, age spots, pigmentation, scarring, blisters, boils, cysts, pimples, cuts, scratches, burns, abrasions, splinters, insect bites and stings, animal bites and scratches, ulcers, loss of elasticity or collagen, wrinkles, sagging skin, acne, measles, chicken pox, and the presence of pathogens and microbes on the skin that is an inevitable consequence of daily life. Based on the result of laboratory testing, it is expected that the copper ion treatments will kill bacteria causing bacterial vaginosis, gonorrhea and chlamydia, and the viruses responsible for Herpes (I and II) and HIV at a kill rate of 99.99 percent in 6 hours. Accordingly, the copper ion treatments are sufficiently effective to "cure" the diseases and conditions described herein and to prevent the occurrence or development of such diseases and conditions. Similarly, copper has been demonstrated as having the capability to kill or render inactive *staphylococcus, streptococcus, enterobacter*, trichomonas, *E. coli* and *pseudomonas*. The copper ion treatments are highly effective at treating the various abnormal or undesired body conditions while being safe and non-toxic. In particular, copper toxicity is so rare that the World Health Organization (WHO) has determined that there is no need for setting an upper threshold for the ingestion of copper. The copper ion treatments can thus be safety used without concern for overdosing or improper use. Moreover, it is believed that, to date, no bacteria or other harmful microorganisms have been found to be capable of developing a resistance to copper, in contrast to the many bacteria and organisms that have developed or are in the process of developing resistance to conventional antibiotics. The multi-target effects of copper makes bacterial resistance extremely unlikely as copper kills bacteria very quickly and leaves almost no survivors. Consequently, there is neither the time for bacteria to "learn" how to resist the killing effect of copper or the possibilty to pass on any knowledge to a significant population of survivors. The copper ion treatments provide a degree of efficacy and safety for treating a wide array of diseases and body conditions that far surpasses conventional pharmaceutical and non-pharmaceutical products and drugs available for treating the same conditions.

According to an aspect of the invention, conditions affecting the oral area of the body, i.e. mouth, throat and airway, are treated by spraying the copper ion-containing solution onto anatomical tissue within the oral cavity as described below in Example 33 which utilizes the copper ion-containing solution prepared in accordance with Example 1. However, the other copper ion-containing solutions could be used in the method of Example 33. The method set forth in Example 33 can be carried out using the devices 10 or 20 of FIGS. 1 and 2 to spray the copper ion-containing solution onto anatomical tissue in the oral cavity, although the device 20 of FIG. 2 may be preferable when treating conditions affecting the throat, tonsils and airway due to its ability to reach deeper into the oral cavity.

Example 33

As soon as possible following diagnosis or the onset of symptoms spray the throat with the copper ion-containing solution using two consecutive pumps of the spray pump nozzle 14 or 24 to deliver to the throat a dose of the copper ion-containing solution corresponding to two sprays of the copper ion-containing solution from the nozzle. Avoid eating or drinking for at least 30 minutes, and preferably one hour, after spraying the throat with the copper ion-containing solution. Repeat every four hours for a number of consecutive days.

The number of consecutive days that the method of Example 33 should be carried out can be based on the advice of a medical professional in accordance with the condition or conditions being treated, the severity of the condition or conditions, and patient history. Typically, the method should be carried out for 5 to 7 consecutive days, most preferably 7 consecutive days, but the method could be carried out for a longer period of time when treating more serious or stubborn conditions. As a result of the copper ions in the copper ion-containing solution contacting anatomical tissue of the throat and oral cavity and mixing with the saliva found in the oral cavity, local (oral) and systemic effects are realized including antibacterial, antimicrobial, antiseptic, antifungal, antiviral, anti-pathogenic, anti-inflammatory, spermicidal, neutralization of free radicals, promotion of healing and tissue repair, prevention of biofilm, and immune-boosting effects. The method of Example 33 is particularly advantageous for treating conditions affecting the oral area including one or more of colds, sore throat, tonsillitis, cough, bronchitis, allergies, hoarseness and laryngitis. The method set forth in Example 33 can also be used to treat conditions including one or more of *streptococcus, staphylococcus, trichomonas*, fungal diseases, thrush, herpes (I and II), HIV, HPV, chlamydia and gonorrhea when such conditions affect or occur in the oral cavity.

A method of treating canker sores, mouth sores and mouth ulcers affecting anatomical tissue in the oral cavity is described below in Example 34. The method of Example 34 utilizes the copper ion-containing solution prepared in accordance with Example 1; however, the other copper ion-containing solutions could be used. The method of Example 34 may best be carried out using the device 10 of FIG. 1 to dispense the copper ion-containing solution.

Example 34

As soon as possible following the first symptom of a canker sore, mouth sore or mouth ulcer on anatomical tissue in the oral cavity, spray the canker sore, mouth sore or mouth ulcer directly with the copper ion-containing solution using two consecutive pumps of the spray pump nozzle 14 to deliver to the canker sore, mouth sore or mouth ulcer a dose of the copper ion-containing solution corresponding to two sprays of the copper ion-containing solution from the nozzle. Avoid eating or drinking for at least 30 minutes, and preferably one hour, after spraying the canker sore, mouth sore or mouth ulcer with the copper ion-containing solution. Repeat every two hours until the canker sore, mouth sore or mouth ulcer has healed.

When carrying out Example 34, the outlet orifice 16 of the spray pump nozzle 14 should be positioned close to the canker sore, mouth sore or mouth ulcer being treated so that the sprays of copper ion-containing solution are concentrated on the canker sore, mouth sore or mouth ulcer. As with Example 33, the copper ions contacting the affected anatomical tissue and mixing with saliva bring about local and systemic therapeutic effects. Although Examples 33 and 34 may best be carried out by spraying the copper ion-containing solution onto the anatomical tissue in the oral cavity, it should be appreciated that the copper ion-containing solution could be delivered to the anatomical tissue in the oral cavity using the swab 105 of FIG. 11. In this case, the swab 105 can be saturated with the copper ion-containing solution, and handle 103 can be manipulated to contact the anatomical tissue within the oral cavity with the swab 105 such that the copper ion-containing solution is deposited on or transferred to such tissue.

According to another aspect of the invention, conditions affecting the respiratory area of the body, i.e. nose, nasal passages and sinuses, are treated by delivering the copper ion-containing solution into the nostrils as described below in Examples 35 and 36. Examples 35 and 36 utilize the copper ion-containing solution of Example 1, but the other copper ion-containing solutions could be utilized. The methods of Examples 35 and 36 can best be carried out using the device 30 of FIG. 3 to deliver the copper ion-containing solution into the nostrils in the form of spray (Example 35) or drops (Example 36). However, the copper ion-containing solution could be delivered to the nasal passages by swabbing the nasal passages with the solution using the device 101.

Example 35

As soon as possible following diagnosis or the onset of symptoms, spray the copper ion-containing solution inside a nostril using two consecutive squeezes of the container 32 to deliver to the nostril a dose of the copper ion-containing solution corresponding to two sprays of the copper ion-containing solution from the outlet orifice 36. Deliver two sprays of the copper ion-containing solution into the other nostril in the same manner. Repeat every four hours for a number of consecutive days.

Example 36

As soon as possible following diagnosis or the onset of symptoms, deliver two drops of the copper ion-containing solution into a nostril using two consecutive squeezes of the container 32 to deliver to the nostril a dose of the copper ion-containing solution corresponding to two drops of the copper ion-containing solution from the outlet orifice 36. Deliver two drops of the copper ion-containing solution to the other nostril in the same manner. Repeat every four hours for a number of consecutive days.

When delivering the copper ion-containing solution to the nostrils by drops as in Example 38, the head should be tilted backwards so that the drops, when dispensed from the dropper 34, flow deeper or farther into the nasal passages. The number of consecutive days that the methods described in Examples 35 and 36 should be repeated can be based on the advice of a medical professional in accordance with the condition or conditions being treated, the severity of the condition or conditions and patient history. Typically, the methods would be carried out for 5 to 7 consecutive days, most preferably 7 consecutive days, although more serious or stubborn conditions may require treatment for a longer period of time. When the copper ion-containing solution is delivered into the nostrils or nasal passages as in Examples 35 and 36, the copper ions come in contact with anatomical tissue within the nasal passages or nostrils and provide local and systemic therapeutic effect as previously described. The methods of Examples 35 and 36 are advantageous for treating conditions affecting the respiratory area including one or more of colds, congestion, nasal discharge, runny nose, allergies, asthma, wheezing, sinusitis, rhinosinusitis, sinus pressure and sneezing.

It is a further aspect of the invention to treat conditions affecting the otic area of the body, i.e. ears, ear canal, outer ear and middle ear. Methods of treating conditions affecting the otic area involve delivering the copper ion-containing solution into the ear canal of an affected ear as described below in Examples 37 and 38. Examples 37 and 38 utilize the copper ion-containing solution of Example 1, but the other copper ion-containing solutions could be used. The methods of Examples 37 and 38 can best be carried out using the device 30 of FIG. 3 to deliver the copper ion-containing solution into the ear canal as drops (Example 37) or as spray (Example 38). However, the copper ion-containing solution could be delivered to the ear canal by swabbing the ear canal with the solution using the device 101.

Example 37

As soon as possible following diagnosis or the onset of symptoms, deliver two drops of the copper ion-containing solution into the ear canal of an affected ear using two consecutive squeezes of the container 32 to deliver to the ear canal a dose of the copper ion-containing solution corresponding to two drops of the copper ion-containing solution from the outlet orifice 36, if the opposite ear is also affected, deliver two drops of the copper ion-containing solution to the ear canal of the opposite ear in the same manner. Repeat every four hours for a number of consecutive days.

Example 38

As soon as possible following diagnosis or the onset of symptoms, spray the copper ion-containing solution inside the ear canal of an affected ear using two consecutive squeezes of the container 32 to deliver to the ear canal a dose of the copper ion-containing solution corresponding to two sprays of the copper ion-containing solution from the outlet orifice 36. If the opposite ear is also affected, deliver two sprays of the copper ion-containing solution to the ear canal of the opposite ear in the same manner. Repeat every four hours for a number of consecutive days.

When carrying out the methods of Examples 37 and 38, the dropper 34 (Example 37) or extension 34 (Example 38) should be inserted in the ear canal as far as possible without causing any discomfort. The number of consecutive days that the methods of Examples 37 and 38 should be carried out may be based on the advice of a medical professional in accordance with the underlying condition or conditions being treated, the severity of the condition or conditions and patient history. Typically, the methods will be carried out for 5 to 7 consecutive days, most preferably 7 consecutive days, but longer periods of treatment may be warranted. When the copper ion-containing solution is delivered into the ear canals as in Examples 37 and 38, the copper ions come in contact with anatomical tissue in the ear and provide the therapeutic effects previously described. The methods of Examples 37 and 38 are advantageous for treating conditions affecting the otic area including one or more of earache, ear infection, stuffy ears and pressure in the ears.

A method of treating conditions, including inflammation, infection or disease, affecting the gums is described below in Example 39. The method of Example 39 utilizes the copper ion-containing solution prepared in accordance with Example 1; however, the other copper ion-containing solutions could be used. The method of Example 39 involves spraying the copper ion-containing solution on the affected area of the gums and may be best carried out using the device 10. This method can also be adapted to treat halitosis or bad breath.

Example 39

As soon as possible following the diagnosis or onset of symptoms, spray the affected area of the gums with the copper ion-containing solution using two consecutive pumps of the spray pump nozzle 14 to deliver to the affected area of the gums a dose of the copper ion-containing solution corresponding to two sprays of the copper ion-containing solution from the nozzle. Avoid eating or drinking for at least 30 minutes, and preferably one hour, after spraying the affected area. Repeat every two hours until the inflammation, infection or disease has resolved.

Yet another aspect of the invention involves using the copper ion-containing solution as a treatment for bad breath or halitosis, and tooth decay. Example 40 describes a method for treating halitosis using a copper ion mouthwash containing the copper ion-containing solution as described in Example 22. This method is also useful for treating inflammation, infection or disease affecting the gums, and tooth decay. The copper ion mouthwash would be supplied an a bottle with a removable cap into which a predetermined quantity or dose of the copper ion mouthwash can be poured and the cap then used as a cup to deliver the copper ion mouthwash to the mouth in a conventional manner of using mouthwashes.

Example 40

Gargle or rinse the mouth with a capful of the copper ion mouthwash in the morning and again in the evening every day on a regular basis.

Another method for treating halitosis involves using a copper ion toothpaste containing the copper ion-containing solution as described in Example 21. In addition to treating halitosis, this method is also useful for treating inflammation, infection or disease affecting the gums, and tooth decay.

Example 41

Brush the teeth with the copper ion toothpaste in the morning and again in the evening every day on a regular basis.

When the methods of Examples 39, 40 and 41 are carried out, copper ions contact anatomical tissue in the oral cavity and mingle with the saliva in the oral cavity, thereby providing the local and systemic therapeutic effects previously described. The antibacterial effects brought about by the copper ions results in the elimination, reduction and/or prevention of halitosis and tooth decay since halitosis and tooth decay are caused primarily by bacteria and the degradation of bacteria in the oral cavity. When using the method of Example 39 to treat halitosis, the copper ion-containing solution should be sprayed on the tongue and on the insides of the cheeks. While the methods described in Examples 39, 40 and 41 are effective to treat halitosis, tooth decay, as well as inflammation, infection or disease affecting the gums, these methods are also useful to indirectly treat other conditions affecting the oral cavity due to the fact that the copper ions will reduce the level of harmful pathogens, microbes, bacteria, viruses and fungi in the mouth.

The conditions affecting the oral cavity that are treatable with the copper ion-containing solutions, copper ion toothpastes and mouthwashes in accordance with the methods described above include one or more of colds, bronchitis, allergies, tonsillitis, sneezing, cough, hoarseness, laryngitis, sore gums, inflamed gums, infected gums, periodontal disease, bad breath, tooth decay, gonorrhea, chlamydia, *streptococcus, staphylococcus, trichomonas*, herpes (I and II), HPV, HIV, canker sores, mouth sores and mouth ulcers. The diseases or conditions affecting the respiratory areas that are treatable with the copper ion-containing solutions include one or more of colds, sinusitis, rhinosinusitis, nasal discharge, congestion, runny nose, allergies, asthma, wheezing and generalized infections of bacterial, viral and/or fungal origin. The conditions affecting the otic areas that are treatable with the copper ion-containing solutions include ear infections, earache, pressure in the ears and stuffy ears. The methods of treatment are particularly beneficial for treating active inflammation, irritation, infection or disease in the oral, respiratory and/or otic areas, and for presenting the development of diseases and undesired body conditions in the oral, respiratory and/or otic areas.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of treating conditions affecting the oral cavity, consisting of the steps of
    spraying into the oral cavity a copper ion-containing solution consisting of copper ions, a biocompatible saline solution, and a buffer, wherein the buffer has a pH of 5±0.4, wherein the copper ions are disposed in the copper ion-containing solution as a result of leaching the copper ions from a solid copper metal disposed in the biocompatible saline solution and buffer, wherein the solid copper metal is a copper alloy, and wherein the buffer is a biocompatible solution consisting of a solvent, acetic acid, and acetate; and repeating said step of spraying for a number of consecutive days.

2. The method of treating recited in claim 1 wherein said step of spraying includes spraying the copper ion-containing solution from a spray pump nozzle into a throat.

3. The method of treating recited in claim 1 wherein said step of spraying includes spraying the copper ion-containing solution from a spray pump nozzle onto a canker sore, mouth sore or mouth ulcer within the oral cavity.

4. The method of treating recited in claim 1 wherein said step of spraying includes spraying the copper ion-containing solution from a spray pump nozzle onto a gum area that is sore, inflamed, or infected.

5. The method of treating recited in claim 1 wherein the conditions treated include bacterial, viral and/or fungal conditions.

6. The method of treating recited in claim 1 wherein spraying the copper ion-containing solution into the oral cavity kills bacteria, virus, and fungus present in the oral cavity.

7. The method of treating recited in claim 1, wherein the concentration of copper ions is between 0.04 mg/ml and 0.209 mg/ml.

8. The method of treating recited in claim 1, wherein the copper alloy is selected from the group consisting of a brass, a bronze, a copper-nickel, and a copper-nickel-zinc.

9. A method of treating conditions affecting the oral cavity, consisting of the steps of:
spraying into the oral cavity a copper ion-containing solution consisting of copper ions, a biocompatible saline solution, and a buffer comprising at least one of acetate and acetic acid, wherein the buffer has a pH of 5±0.4, wherein the copper ions are disposed in the copper ion-containing solution as a result of leaching the copper ions from a solid copper metal disposed in the biocompatible saline solution and buffer, wherein the solid copper metal is a copper alloy, and wherein the copper ion-containing solution is free or substantially free of active ingredients other than copper ions; and repeating said step of spraying for a number of consecutive days.

10. The method of treating recited in claim 9, wherein the copper alloy is selected from the group consisting of a brass, a bronze, a copper-nickel, and a copper-nickel-zinc.

11. The method of treating recited in claim 9 wherein said step of spraying includes spraying the copper ion-containing solution from a spray pump nozzle into a throat.

12. The method of treating recited in claim 9 wherein said step of spraying includes spraying the copper ion-containing solution from a spray pump nozzle onto a canker sore, mouth sore, or mouth ulcer within the oral cavity.

13. The method of treating recited in claim 9 wherein said step of spraying includes spraying the copper ion-containing solution from a spray pump nozzle onto a gum area that is sore, inflamed, or infected.

14. The method of treating recited in claim 9 wherein the conditions treated include bacterial, viral, and/or fungal conditions.

15. The method of treating recited in claim 10 wherein spraying the copper ion-containing solution into the oral cavity kills bacteria, virus, and fungus present in the oral cavity.

16. The method of treating recited in claim 9, wherein the concentration of copper ions is between 0.04 mg/ml and 0.209 mg/ml.

* * * * *

UNITED STATES PATENT AND TRADEMARK OFFICE
CERTIFICATE OF CORRECTION

| | | |
|---|---|---|
| PATENT NO. | : 11,298,316 B2 | |
| APPLICATION NO. | : 17/231764 | |
| DATED | : April 12, 2022 | |
| INVENTOR(S) | : ChunLim Abbott et al. | |

It is certified that error appears in the above-identified patent and that said Letters Patent is hereby corrected as shown below:

In the Claims

Please correct Column 30 Line 28 Claim 15 to read as:
15. The method of treating recited in claim 9 wherein spraying the copper ion-containing solution into the oral cavity kills bacteria, virus, and fungus present in the oral cavity.

Signed and Sealed this
Thirty-first Day of May, 2022

*Katherine Kelly Vidal*

Katherine Kelly Vidal
*Director of the United States Patent and Trademark Office*